(12) United States Patent
Robertson et al.

(10) Patent No.: US 9,999,603 B2
(45) Date of Patent: Jun. 19, 2018

(54) COMPOSITIONS AND METHODS INCLUDING LEELAMINE AND ARACHIDONYL TRIFLUOROMETHYL KETONE RELATING TO TREATMENT OF CANCER

(71) Applicant: The Penn State Research Foundation, University Park, PA (US)

(72) Inventors: Gavin P. Robertson, Hummelstown, PA (US); Omer F. Kuzu, Harrisburg, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days. days.

(21) Appl. No.: 14/777,023

(22) PCT Filed: Mar. 15, 2013

(86) PCT No.: PCT/US2013/032245
§ 371 (c)(1),
(2) Date: Sep. 15, 2015

(87) PCT Pub. No.: WO2014/142995
PCT Pub. Date: Sep. 18, 2014

(65) Prior Publication Data
US 2016/0030366 A1   Feb. 4, 2016

(51) Int. Cl.
*A61K 31/135* (2006.01)
*A61K 31/121* (2006.01)
*A61K 9/127* (2006.01)

(52) U.S. Cl.
CPC .......... *A61K 31/135* (2013.01); *A61K 9/1271* (2013.01); *A61K 31/121* (2013.01)

(58) Field of Classification Search
None
See application file for complete search history.

(56) References Cited

U.S. PATENT DOCUMENTS

| | | | | |
|---|---|---|---|---|
| 2008/0262286 A1* | 10/2008 | Hallahan | ............... | A61K 31/66 600/1 |
| 2012/0082659 A1* | 4/2012 | Land | ..................... | A61K 31/00 424/130.1 |
| 2012/0141578 A1* | 6/2012 | Robertson | ............ | A61K 9/0019 424/450 |

OTHER PUBLICATIONS

Torchilin, V. et al., Structure and design of polymeric surfactant-based drug delivery systems, *Journal of Controlled Release*, 73(2-3): 137-72, Jun. 15, 2001.

* cited by examiner

*Primary Examiner* — Celeste A Roney
(74) *Attorney, Agent, or Firm* — Dinsmore & Shohl LLP

(57) ABSTRACT

The present invention relates to compositions and methods for treatment of proliferative disease. In specific aspects, the present invention relates to compositions including (1R,4aS,10aR)-1,2,3,4,4a,9,10,10a-octahydro-1-,4a-dimethyl-7-(1-methylethyl)-1-phenanthrenemethanamine (leelamine) and arachidonyl trifluoromethyl ketone (ATK) in combination; methods for treatment of cancer including administration of leelamine and ATK in a subject in need thereof; and particularly methods for treatment of skin cancer including administration of leelamine and ATK in a subject in need thereof.

13 Claims, 20 Drawing Sheets heated liposomal ATK

|  | Diam. (nm) | % Int. | Width (nm) | MW (kDa) | Width (kDa) | Start (mL) | End (mL) |
|---|---|---|---|---|---|---|---|
| Peak 1: | 120.6 | 100.0 | 63.82 | 4.93e4 | 1.11e4 | 0.00 | 0.00 |
| Peak 2: | 0.000 | 0.0 | 0.000 | 0.00 | 0.00 | 0.00 | 0.00 |
| Peak 3: | 0.000 | 0.0 | 0.000 | 0.00 | 0.00 | 0.00 | 0.00 |

| | | Mean (mV) | Area (%) | Width (mV) |
|---|---|---|---|---|
| Zeta Potential (mV): -45.6 | Peak 1: | -45.6 | 100.0 | 7.75 |
| Zeta Deviation (mV): 7.75 | Peak 2: | 0.00 | 0.0 | 0.00 |
| Conductivity (mS/cm): 0.0412 | Peak 3: | 0.00 | 0.0 | 0.00 |

Result quality : Good

COMPOSITIONS AND METHODS INCLUDING LEELAMINE AND ARACHIDONYL TRIFLUOROMETHYL KETONE RELATING TO TREATMENT OF CANCER

GRANT REFERENCE

This invention was made with government support under Grant Nos. CA127892, CA136667 and CA138634, awarded by the National Institutes of Health. The Government has certain rights in the invention.

FIELD OF THE INVENTION

The present invention relates to compositions and methods for treatment of proliferative disease. In specific aspects, the present invention relates to compositions including (1R, 4aS,10aR)-1,2,3,4,4a,9,10,10a-octahydro-1-,4a-dimethyl-7-(1-methylethyl)-1-phenanthrenemethanamine (leelamine) and arachidonyl trifluoromethyl ketone (ATK) in combination; methods for treatment of a proliferative disease including administration of leelamine and ATK in a subject in need thereof; and particularly methods for treatment of skin cancer including administration of leelamine and ATK in a subject in need thereof.

BACKGROUND OF THE INVENTION

In spite of recent medical progress, cancer continues to be one of the most common and deadly diseases. There is a continuing need for compositions and methods to treat cancer.

SUMMARY OF THE INVENTION

Pharmaceutical compositions are provided according to aspects of the present invention which include leelamine; arachidonyl trifluoromethyl ketone; and a pharmaceutically acceptable carrier.

Pharmaceutical compositions are provided according to aspects of the present invention which include leelamine and arachidonyl trifluoromethyl ketone contained together in liposomes.

Pharmaceutical compositions are provided according to aspects of the present invention which include leelamine and arachidonyl trifluoromethyl ketone contained together in liposomes, wherein the liposomes have an average particle size in the range of 1 nm-500 nm.

Pharmaceutical compositions are provided according to aspects of the present invention which include leelamine and arachidonyl trifluoromethyl ketone contained together in liposomes, wherein the liposomes have an average particle size in the range of 20 nm-250 nm.

Pharmaceutical compositions are provided according to aspects of the present invention which include leelamine and arachidonyl trifluoromethyl ketone contained together in liposomes, wherein the liposomes have an average particle size in the range of 50 nm-150 nm.

Pharmaceutical compositions are provided according to aspects of the present invention which include leelamine and arachidonyl trifluoromethyl ketone contained together in liposomes, wherein the ratio of leelamine:arachidonyl trifluoromethyl ketone is in the range of 1:100-100:1 and wherein the liposomes have an average particle size in the range of 1 nm-500 nm, 20 nm-250 nm or 50 nm-150 nm.

Pharmaceutical compositions are provided according to aspects of the present invention which include leelamine and arachidonyl trifluoromethyl ketone contained together in liposomes, wherein the ratio of leelamine:arachidonyl trifluoromethyl ketone is in the range of 1:50-50:1 and wherein the liposomes have an average particle size in the range of 1 nm-500 nm, 20 nm-250 nm or 50 nm-150 nm.

Pharmaceutical compositions are provided according to aspects of the present invention which include leelamine and arachidonyl trifluoromethyl ketone contained together in liposomes, wherein the ratio of leelamine:arachidonyl trifluoromethyl ketone is in the range of 1:1-1:50 and wherein the liposomes have an average particle size in the range of 1 nm-500 nm, 20 nm-250 nm or 50 nm-150 nm.

Pharmaceutical compositions are provided according to aspects of the present invention which include leelamine and arachidonyl trifluoromethyl ketone contained together in liposomes, wherein the ratio of leelamine:arachidonyl trifluoromethyl ketone is in the range of 1:10-1:20 and wherein the liposomes have an average particle size in the range of 1 nm-500 nm, 20 nm-250 nm or 50 nm-150 nm.

Pharmaceutical compositions are provided according to aspects of the present invention which include leelamine and arachidonyl trifluoromethyl ketone contained together in liposomes, wherein the leelamine is present in a concentration in the range of 0.1 micromolar-100 millimolar and the arachidonyl trifluoromethyl ketone is present in a concentration in the range of 0.1 micromolar-100 millimolar and wherein the liposomes have an average particle size in the range of 1 nm-500 nm, 20 nm-250 nm or 50 nm-150 nm.

Pharmaceutical compositions are provided according to aspects of the present invention which include leelamine and arachidonyl trifluoromethyl ketone contained together in liposomes, wherein the leelamine is present in a concentration in the range of 0.5 micromolar-10 millimolar and the arachidonyl trifluoromethyl ketone is present in a concentration in the range of 0.5 micromolar-10 millimolar and wherein the liposomes have an average particle size in the range of 1 nm-500 nm, 20 nm-250 nm or 50 nm-150 nm.

Pharmaceutical compositions are provided according to aspects of the present invention which include leelamine and arachidonyl trifluoromethyl ketone contained together in liposomes, wherein the leelamine is present in a concentration in the range of 0.75 micromolar-1 millimolar and the arachidonyl trifluoromethyl ketone is present in a concentration in the range of 0.75 micromolar-1 millimolar and wherein the liposomes have an average particle size in the range of 1 nm-500 nm, 20 nm-250 nm or 50 nm-150 nm.

Pharmaceutical compositions are provided according to aspects of the present invention which include leelamine and arachidonyl trifluoromethyl ketone contained together in liposomes, wherein the leelamine is present in a concentration in the range of 1 micromolar-100 micromolar and the arachidonyl trifluoromethyl ketone is present in a concentration in the range of 1 micromolar-100 micromolar and wherein the liposomes have an average particle size in the range of 1 nm-500 nm, 20 nm-250 nm or 50 nm-150 nm.

Pharmaceutical compositions are provided according to aspects of the present invention which include leelamine and arachidonyl trifluoromethyl ketone contained together in liposomes, wherein the leelamine is present in a concentration in the range of 0.1 micromolar-50 micromolar and the arachidonyl trifluoromethyl ketone is present in a concentration in the range of 2.5 micromolar-1250 micromolar and wherein the liposomes have an average particle size in the range of 1 nm-500 nm, 20 nm-250 nm or 50 nm-150 nm.

Pharmaceutical compositions are provided according to aspects of the present invention which include arachidonyl trifluoromethyl ketone contained in liposomes.

Pharmaceutical compositions are provided according to aspects of the present invention which include arachidonyl trifluoromethyl ketone contained in liposomes and wherein the liposomes have an average particle size in the range of 1 nm-500 nm, 20 nm-250 nm or 50 nm-150 nm.

Pharmaceutical compositions are provided according to aspects of the present invention which include arachidonyl trifluoromethyl ketone contained in liposomes, wherein the liposomes have an average particle size in the range of 1 nm-500 nm, 20 nm-250 nm or 50 nm-150 nm and wherein the arachidonyl trifluoromethyl ketone is present in a concentration in the range of 0.1 micromolar-100 millimolar.

Pharmaceutical compositions are provided according to aspects of the present invention which include arachidonyl trifluoromethyl ketone contained in liposomes, wherein the liposomes have an average particle size in the range of 1 nm-500 nm, 20 nm-250 nm or 50 nm-150 nm and wherein the arachidonyl trifluoromethyl ketone is present in a concentration in the range of 0.5 micromolar-10 millimolar.

Pharmaceutical compositions are provided according to aspects of the present invention which include arachidonyl trifluoromethyl ketone contained in liposomes, wherein the liposomes have an average particle size in the range of 1 nm-500 nm, 20 nm-250 nm or 50 nm-150 nm and wherein the arachidonyl trifluoromethyl ketone is present in a concentration in the range of 0.75 micromolar-1 millimolar.

Pharmaceutical compositions are provided according to aspects of the present invention which include arachidonyl trifluoromethyl ketone contained in liposomes, wherein the liposomes have an average particle size in the range of 1 nm-500 nm, 20 nm-250 nm or 50 nm-150 nm and wherein the arachidonyl trifluoromethyl ketone is present in a concentration in the range of 1 micromolar-100 micromolar.

Pharmaceutical compositions are provided according to aspects of the present invention which include arachidonyl trifluoromethyl ketone contained in liposomes, wherein the liposomes have an average particle size in the range of 1 nm-500 nm, 20 nm-250 nm or 50 nm-150 nm and wherein the arachidonyl trifluoromethyl ketone is present in a concentration in the range of 2.5 micromolar-1250 micromolar.

Pharmaceutical compositions are provided according to the present invention which include liposomes containing leelamine, liposomes containing arachidonyl trifluoromethyl ketone, or liposomes containing both leelamine and arachidonyl trifluoromethyl ketone, wherein the liposomes include at least one polyethylene glycol modified neutral lipid, wherein the amount of polyethylene glycol modified neutral lipid is an amount in the range of 2.5-30 molar percent, inclusive, of total lipids in the liposomes; and one or more anionic, cationic or neutral lipids in an amount in the range of 70-97.5, inclusive, molar percent of total lipids in the liposomes.

Pharmaceutical compositions are provided according to the present invention which include liposomes containing leelamine, liposomes containing arachidonyl trifluoromethyl ketone, or liposomes containing both leelamine and arachidonyl trifluoromethyl ketone, wherein the liposomes include at least one polyethylene glycol modified neutral lipid, wherein the amount of polyethylene glycol modified neutral lipid is an amount in the range of 5-20 molar percent, inclusive, of total lipids in the liposomes; and one or more anionic, cationic or neutral lipids in an amount in the range of 80-95, inclusive, molar percent of total lipids in the liposomes.

Pharmaceutical compositions are provided according to the present invention which include liposomes containing leelamine, liposomes containing arachidonyl trifluoromethyl ketone, or liposomes containing both leelamine and arachidonyl trifluoromethyl ketone, wherein the liposomes include 1,2-dipalmitoyl-sn-glycero-3-phosphoethanolamine-N-[methoxy(polyethyl glycol)-200], wherein the amount of 1,2-dipalmitoyl-sn-glycero-3-phosphoethanolamine-N-[methoxy(polyethyl glycol)-200] is in the range of 2.5-30 molar percent, inclusive, of total lipids in the liposomes; and L-alpha-phosphatidylcholine in an amount in the range of 70-97.5, inclusive, molar percent of total lipids in the liposomes.

Pharmaceutical compositions are provided according to the present invention which include liposomes containing leelamine, liposomes containing arachidonyl trifluoromethyl ketone, or liposomes containing both leelamine and arachidonyl trifluoromethyl ketone, wherein the liposomes include 1,2-dipalmitoyl-sn-glycero-3-phosphoethanolamine-N-[methoxy(polyethyl glycol)-200], wherein the amount of 1,2-dipalmitoyl-sn-glycero-3-phosphoethanolamine-N-[methoxy(polyethyl glycol)-200] is in the range of 5-20 molar percent, inclusive, of total lipids in the liposomes; and L-alpha-phosphatidylcholine in an amount in the range of 80-95, inclusive, molar percent of total lipids in the liposomes.

Methods of treating cancer in a subject in need thereof are provided according to aspects of the present invention which include administering, concurrently or sequentially, a therapeutically effective amount of leelamine and arachidonyl trifluoromethyl ketone to the subject.

Methods of treating cancer in a subject in need thereof are provided according to aspects of the present invention which include administering, concurrently, a therapeutically effective amount of leelamine and arachidonyl trifluoromethyl ketone to the subject.

Methods of treating cancer in a subject in need thereof are provided according to aspects of the present invention which include administering, sequentially, a therapeutically effective amount of leelamine and arachidonyl trifluoromethyl ketone to the subject.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are administered together in a single formulation.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the leelamine is present in a concentration in the range of 0.1 micromolar-100 millimolar and the arachidonyl trifluoromethyl ketone is present in a concentration in the range of 0.1 micromolar-100 millimolar, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the leelamine is present in a concentration in the range of 0.5 micromolar-10 millimolar and the arachidonyl trifluoromethyl ketone is present in a concentration in the range of 0.5 micromolar-10 millimolar, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the leelamine is present in a concentration in the range of 0.75 micromolar-1 millimolar and the arachidonyl trifluoromethyl ketone is present in a concentration in the range of 0.75 micromolar-1 millimolar and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the leelamine is present in a concentration in the range of 1 micromolar-100 micromolar and the arachidonyl trifluoromethyl ketone is present in a concentration in the range of 1 micromolar-100 micromolar, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the leelamine is present in a concentration in the range of 0.1 micromolar-50 micromolar and the arachidonyl trifluoromethyl ketone is present in a concentration in the range of 2.5 micromolar-1250 micromolar, and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the ratio of leelamine:arachidonyl trifluoromethyl ketone is in the range of 1:100-100:1 and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the ratio of leelamine:arachidonyl trifluoromethyl ketone is in the range of 1:50-50:1 and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the ratio of leelamine:arachidonyl trifluoromethyl ketone is in the range of 1:1-1:50 and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine and arachidonyl trifluoromethyl ketone are contained together in liposomes, wherein the ratio of leelamine:arachidonyl trifluoromethyl ketone is in the range of 1:10-1:20 and wherein the liposomes have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, and wherein the leelamine and/or arachidonyl trifluoromethyl ketone are administered concurrently or sequentially.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, and wherein the liposomes containing leelamine without arachidonyl trifluoromethyl ketone and liposomes containing arachidonyl trifluoromethyl ketone without leelamine have an average particle size in the range of 1 nm-500 nm, 20 nm-250 nm or 50 nm-150 nm.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the ratio of leelamine: arachidonyl trifluoromethyl ketone administered is in the range of 1:100-100:1.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the ratio of leelamine: arachidonyl trifluoromethyl ketone administered is in the range of 1:50-50:1.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the ratio of leelamine: arachidonyl trifluoromethyl ketone administered is in the range of 1:1-1:50.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the ratio of leelamine: arachidonyl trifluoromethyl ketone administered is in the range of 1:10-1:20.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the leelamine is administered in a concentration in the range of 0.1 micromolar-100 millimolar and the arachidonyl trifluoromethyl ketone is administered in a concentration in the range of 0.1 micromolar-100 millimolar.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the leelamine is present in a concentration in the range of 0.5 micromolar-10 millimolar and the arachidonyl trifluoromethyl ketone is present in a concentration in the range of 0.5 micromolar-10 millimolar.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the leelamine is present in a concentration in the range of 0.75 micromolar-1 millimolar and the arachidonyl trifluoromethyl ketone is present in a concentration in the range of 0.75 micromolar-1 millimolar.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the leelamine is present in a concentration in the range of 1 micromolar-100 micromolar and the arachidonyl trifluoromethyl ketone is present in a concentration in the range of 1 micromolar-100 micromolar.

Methods of treating cancer in a subject in need thereof are provided according to aspects of the present invention which include administering a pharmaceutical composition including a therapeutically effective amount of leelamine and arachidonyl trifluoromethyl ketone to the subject, wherein the leelamine is contained in liposomes without arachidonyl trifluoromethyl ketone, arachidonyl trifluoromethyl ketone is contained in liposomes without leelamine or both arachidonyl trifluoromethyl ketone and leelamine are separately contained in liposomes, wherein the leelamine and/or arachidonyl trifluoromethyl ketone are administered concurrently or sequentially, and wherein the leelamine is present in a concentration in the range of 0.1 micromolar-50 micromolar and the arachidonyl trifluoromethyl ketone is present in a concentration in the range of 2.5 micromolar-1250 micromolar.

Methods of treating cancer in a subject in need thereof are provided according to aspects of the present invention which include administering a pharmaceutical composition including liposomes containing leelamine, liposomes containing arachidonyl trifluoromethyl ketone, or liposomes containing both leelamine and arachidonyl trifluoromethyl ketone, wherein the liposomes include at least one polyethylene glycol modified neutral lipid, wherein the amount of polyethylene glycol modified neutral lipid is an amount in the range of 2.5-30 molar percent, inclusive, of total lipids in the liposomes; and one or more anionic, cationic or neutral lipids in an amount in the range of 70-97.5, inclusive, molar percent of total lipids in the liposomes.

Methods of treating cancer in a subject in need thereof are provided according to aspects of the present invention which include administering a pharmaceutical composition including liposomes containing leelamine, liposomes containing arachidonyl trifluoromethyl ketone, or liposomes containing both leelamine and arachidonyl trifluoromethyl ketone, wherein the liposomes include at least one polyethylene glycol modified neutral lipid, wherein the amount of polyethylene glycol modified neutral lipid is an amount in the range of 5-20 molar percent, inclusive, of total lipids in the liposomes; and one or more anionic, cationic or neutral lipids in an amount in the range of 80-95, inclusive, molar percent of total lipids in the liposomes.

Methods of treating cancer in a subject in need thereof are provided according to aspects of the present invention which include administering a pharmaceutical composition including liposomes containing leelamine, liposomes containing arachidonyl trifluoromethyl ketone, or liposomes containing both leelamine and arachidonyl trifluoromethyl ketone, wherein the liposomes include 1,2-dipalmitoyl-sn-glycero-3-phosphoethanolamine-N-[methoxy(polyethyl glycol)-200], wherein the amount of 1,2-dipalmitoyl-sn-glycero-3-phosphoethanolamine-N-[methoxy(polyethyl glycol)-200] is in the range of 2.5-30 molar percent, inclusive, of total lipids in the liposomes; and L-alpha-phosphatidylcholine in an amount in the range of 70-97.5, inclusive, molar percent of total lipids in the liposomes.

Methods of treating cancer in a subject in need thereof are provided according to aspects of the present invention which include administering a pharmaceutical composition including liposomes containing leelamine, liposomes containing arachidonyl trifluoromethyl ketone, or liposomes containing both leelamine and arachidonyl trifluoromethyl ketone, wherein the liposomes include 1,2-dipalmitoyl-sn-glycero-3-phosphoethanolamine-N-[methoxy(polyethyl glycol)-200], wherein the amount of 1,2-dipalmitoyl-sn-glycero-3-phosphoethanolamine-N-[methoxy(polyethyl glycol)-200] is in the range of 5-20 molar percent, inclusive, of total lipids in the liposomes; and L-alpha-phosphatidylcholine in an amount in the range of 80-95, inclusive, molar percent of total lipids in the liposomes.

Methods of treating cancer in a subject in need thereof are provided according to aspects of the present invention wherein the leelamine and/or arachidonyl trifluoromethyl ketone are administered by a route selected from: intravenous, intramuscular, subcutaneous, intraperitoneal, oral, otic, rectal, vaginal, topical, parenteral, pulmonary, ocular, nasal, intratumoral and mucosal.

Methods of treating cancer in a subject in need thereof are provided according to aspects of the present invention wherein the leelamine and/or arachidonyl trifluoromethyl ketone are administered by an intravenous route of administration.

Methods of treating cancer in a subject in need thereof are provided according to aspects of the present invention wherein the leelamine and/or arachidonyl trifluoromethyl ketone are administered intratumorally.

Methods of treating cancer in a subject in need thereof are provided according to aspects of the present invention wherein the leelamine and/or arachidonyl trifluoromethyl ketone are administered topically.

Methods of treating cancer in a subject in need thereof are provided according to aspects of the present invention wherein the subject is human.

Methods of treating cancer in a subject in need thereof are provided according to aspects of the present invention wherein the subject has skin cancer.

Methods of treating cancer in a subject in need thereof are provided according to aspects of the present invention wherein the subject has basal cell carcinoma, squamous cell carcinoma or malignant melanoma.

Methods of treating cancer in a subject in need thereof are provided according to aspects of the present invention wherein the cancer is cancer of the liver, prostate, breast, brain, stomach, pancreas, blood cells, uterus, cervix, ovary, lung, colon, or connective tissue.

Methods of treating cancer in a subject in need thereof are provided according to aspects of the present invention which further include administration of an adjunct anti-cancer treatment.

Commercial packages are provided according to aspects of the present invention which include: leelamine; arachidonyl trifluoromethyl ketone; and instructions for use of leelamine and arachidonyl trifluoromethyl ketone in treating cancer in a subject in need thereof.

Commercial packages are provided according to aspects of the present invention which include a pharmaceutical composition including: leelamine, arachidonyl trifluoromethyl ketone and a pharmaceutically acceptable carrier; and instructions for use of leelamine and arachidonyl trifluoromethyl ketone in treating cancer in a subject in need thereof.

Commercial packages are provided according to aspects of the present invention which include a pharmaceutical composition including: leelamine and arachidonyl trifluoromethyl ketone contained together in liposomes; and instructions for use of leelamine and arachidonyl trifluoromethyl ketone in treating cancer in a subject in need thereof.

Commercial packages are provided according to aspects of the present invention which include a pharmaceutical composition including: leelamine contained in liposomes without arachidonyl trifluoromethyl ketone and arachidonyl trifluoromethyl ketone contained in liposomes without leelamine; and instructions for use of leelamine and arachidonyl trifluoromethyl ketone in treating cancer in a subject in need thereof.

DETAILED DESCRIPTION

Figure 1:
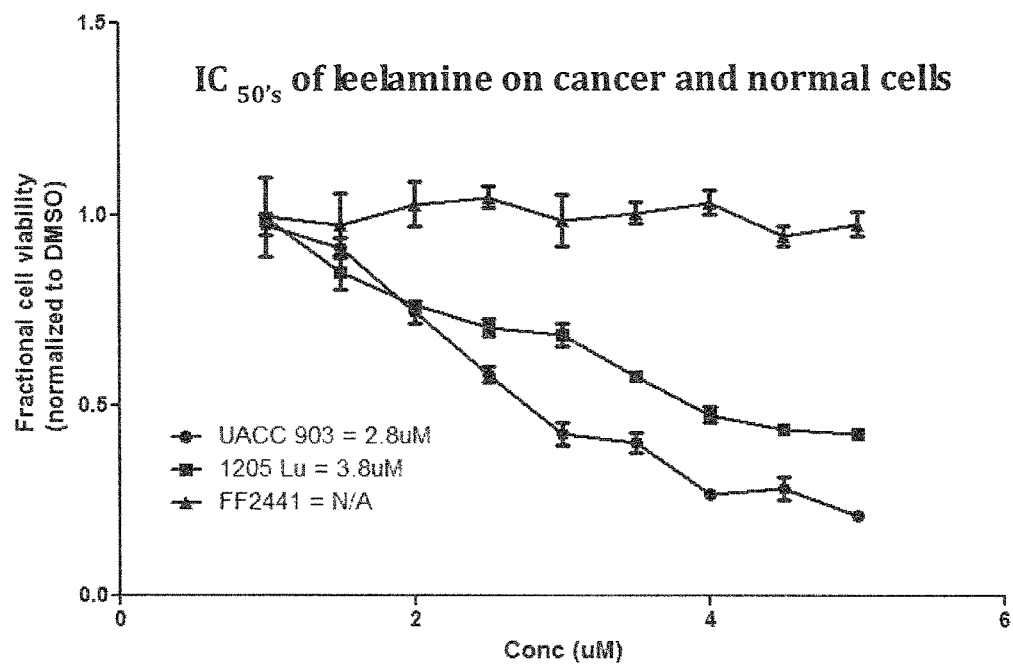
FIG. 1 is a graph showing leelamine treatment provides a dose-dependent decrease in viability of the melanoma cell lines UACC 903 and 1205 Lu, with half-maximal inhibitory concentrations ($IC_{50}$) of 2.8 µM and 3.8 µM, respectively.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2006; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 11th Ed., 2005.

The singular terms "a," "an," and "the" are not intended to be limiting and include plural referents unless explicitly stated otherwise or the context clearly indicates otherwise.

Compositions and methods for treating cancer are provided according to the present invention.

Compositions according to aspects of the present invention prevent and inhibit cancer cell multiplication and tumor development and are considered useful as chemotherapeutic and chemopreventive agents.

(1R,4aS,10aR)-1,2,3,4,4a,9,10,10a-octahydro-1-,4a-dimethyl-7-(1-methylethyl)-1-phenanthrenemethanamine (leelamine) may be obtained commercially, synthesized according to known methods or isolated from natural sources, such as pine tree bark.

Arachidonyl trifluoromethyl ketone (ATK) is an analog of arachidonic acid in which the carboxyl group is replaced with a trifluoromethyl ketone group. ATK inhibits the activity of the 85 kDa cytosolic phospholipase A2 (cPLA2) and the 80 kDa macrophage calcium-independent PLA2 (iPLA2) without altering the activity of the 14 kDa secretory PLA2 (sPLA2). ATK reduces the amount of arachidonic acid (AA) substrate available for the cyclooxygenase enzyme (COX; also known as prostaglandin H synthase) thereby attenuating prostaglandin (PG) synthesis. ATK may be obtained commercially or synthesized according to known methods.

Methods including administration of leelamine and ATK to a subject in need thereof are provided according to particular aspects of the present invention which have utility, for example, in inhibiting cancer cells.

It is appreciated that compositions and methods according to aspects described herein are useful to inhibit cancer cells in vitro and in vivo.

Compositions and Pharmaceutical Compositions

In certain aspects, the present invention relates to compositions including leelamine, compositions including ATK and compositions including both leelamine and ATK.

In certain aspects, the present invention relates to liposomal compositions including leelamine, liposomal compositions including ATK and liposomal compositions including both leelamine and ATK.

Compositions and pharmaceutical compositions including leelamine may be provided as a pharmaceutically acceptable salt, hydrate, amide or ester of leelamine according to aspects of the present invention. Compositions including ATK may be provided as a pharmaceutically acceptable salt, hydrate, amide or ester of ATK according to aspects of the present invention.

Compositions and pharmaceutical compositions according to the present invention encompass stereoisomers of leelamine and ATK. Compositions according to the present invention encompass the individual enantiomers of leelamine and ATK, as well as wholly or partially racemic mixtures of any of these.

Pharmaceutical compositions including ATK and a pharmaceutically acceptable carrier are provided according to aspects of the present invention.

Pharmaceutical compositions including leelamine, ATK and a pharmaceutically acceptable carrier in particular aspects of the present invention.

The term "pharmaceutically acceptable carrier" refers to a carrier which is substantially non-toxic to a subject to which the composition is administered and which is substantially chemically inert with respect to the active component or components.

A pharmaceutical composition according to the invention generally includes about 0.1-99% of leelamine, ATK or both leelamine and ATK.

Advantageously, anti-cancer compounds according to aspects of the present invention are formulated to achieve lipid-solubility and/or aqueous-solubility.

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle, particularly liposomes; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-500 nm, particularly, 20 nm-250 nm and more particularly 50 nm-150 nm.

Aspects of pharmaceutical compositions of the present invention include a lipid-based carrier. The term "lipid-based carrier" refers to macromolecular structures having lipid and/or lipid derivatives as the major constituent.

Lipids included in lipid-based carriers can be naturally-occurring lipids, synthetic lipids or combinations thereof.

A lipid-based carrier is formulated as a liposome for use in compositions, kits and methods according to aspects of the invention. The term "liposome" refers to a bilayer particle of amphipathic lipid molecules enclosing an aqueous interior space. Liposomes are typically produced as small unilammellar vesicles (SUVs), large unilammellar vesicles (LUVs) or multilammellar vesicles (MLVs). Leelamine and/or ATK is associated with liposomes by encapsulation in the aqueous interior space of the liposomes, disposed in the lipid bilayer of the liposomes and/or associated with the liposomes by binding, such as ionic binding or association by van der Waals forces. Thus, leelamine and/or ATK is contained in liposomes when it is encapsulated in the aqueous interior space of the liposomes, disposed in the lipid bilayer of the liposomes and/or associated with the liposomes by binding, such as ionic binding or association by van der Waals forces. Liposomes according to aspects of the invention are generally in the range of about 1 nanometer-1 micron in diameter although they are not limited with regard to size. In particular aspects, liposomes of the present invention have an average particle size in the range of about 1 nm-500 nm, in the range of about 20 nm-250 nm or in the range of about 50 nm-150 nm.

A pharmaceutical composition includes a liposomal formulation of leelamine in particular aspects of the present invention.

A pharmaceutical composition includes a liposomal formulation of ATK in particular aspects of the present invention.

A pharmaceutical composition includes a liposomal formulation of leelamine and ATK in combination in particular aspects of the present invention.

Liposomal formulations of leelamine and/or ATK according to aspects of the present invention include can include one or more types of neutral, cationic lipid and/or anionic lipid, such that the liposomal formulations have a net neutral surface charge at physiological pH. According to aspects, a PEG-modified lipid is included.

The term cationic lipid refers to any lipid which has a net positive charge at physiological pH. Examples of cationic lipids include, but are not limited to, N-(1-(2,3-dioleyloxy) propyl)-N,N,N-trimethylammonium chloride (DOTMA); 1,2-dioleoyloxy-3-(trimethylammonium)propane (DOTAP); 1,2-dioleoyl-3-dimethylammonium-propane (DODAP); dioctadecylamidoglycylspermine (DOGS); 1,2-dipalmitoylphosphatidylethanolamidospermine (DPPES); 2,3-dioleyloxy-N-(2-(sperminecarboxamido)ethyl)-N,N-dimethyl-1-propanaminium trifluoroacetate (DOSPA); dimyristoyltrimethylammonium propane (DMTAP); (3-dimyristyloxypropyl)(dimethyl)(hydroxyethyl)ammonium (DMRIE); dioctadecyldimethylammonium chloride (DODAC), Dimethyldidodecylammonium bromide (DDAB); 3β[N—(N',N'-di methylaminoethane)-carbamoyl] cholesterol (DC-Chol); 1-[2-(9(Z)-octadecenoyloxy)-ethyl]-2-(8(Z)-heptadecenyl)-3-(2-hydroxyethyl)-imidazolinium (DOTIM); bis-guanidinium-spermidine-cholesterol (BGTC); bis-guanidinium-tren-cholesterol (BGTC); 1,3-Dioleoyloxy-2-(6-carboxy-spermyl)-propylamid (DOSPER) N-[3-[2-(1,3-dioleoyloxy)propoxy-carbonyl]propyl]-N,N,N-trimethylammonium iodide (YKS-220); as well as pharmaceutically acceptable salts and mixtures thereof. Additional examples of cationic lipids are described in Lasic and Papahadjopoulos, Medical Applications of Liposomes, Elsevier, 1998; U.S. Pat. Nos. 4,897,355; 5,208,036; 5,264,618; 5,279,833; 5,283,185; 5,334,761; 5,459,127; 5,736,392; 5,753,613; 5,785,992; 6,376,248; 6,586,410; 6,733,777; and 7,145,039.

The term neutral lipid refers to any lipid which has no net charge, either uncharged or in neutral charge zwitterionic form, at physiological pH. Examples of neutral lipids include, but are not limited to, L-alpha-phosphatidylcholine (ePC), distearoylphosphatidylcholine (DSPC), dioleoylphosphatidylethanolamine (DOPE), distearoylphosphatidylethanolamine (DSPE); 1,2-dioleoyl-sn-glycero-3-Phosphocholine (DOPC), 1,2-dipalmitoyl-sn-glycero-3-phosphoethanolamine (DPPE), cephalin, ceramide, cerebrosides, cholesterol, diacylglycerols, and sphingomyelin.

The term anionic lipid refers to any lipid which has a net negative charge at physiological pH. Examples of anionic lipids include, but are not limited to, dihexadecylphosphate (DhP), phosphatidyl inositols, phosphatidyl serines, such as dimyristoyl phosphatidyl serine, and dipalmitoyl phosphatidyl serine, phosphatidyl glycerols, such as dimyristoylphosphatidyl glycerol, dioleoylphosphatidyl glycerol, dilauryloylphosphatidyl glycerol, dipalmitoylphosphatidyl glycerol, distearyloylphosphatidyl glycerol, phosphatidic acids, such as dimyristoyl phosphatic acid and dipalmitoyl phosphatic acid and diphosphatidyl glycerol.

The term "modified lipid" refers to lipids modified to aid in, for example, inhibiting aggregation and/or precipitation, inhibiting immune response and/or improving half-life in circulation in vivo. Modified lipids include, but are not limited to, pegylated lipids, such as polyethyleneglycol 2000 distearoylphosphatidylethanolamine (PEG(2000) DSPE); 1,2-dipalmitoyl-sn-glycero-3-phosphoethanolamine-N-[methoxy(polyethylene glycol)-2000] (DPPE-PEG-2000), and polyethyleneglycol 750 octadecylsphingosine (PEG (750) C8).

Exemplary ratios of lipid components included in liposomal formulations of the present invention are neutral lipid: polyethyleneglycol modified neutral lipid-80:20 mol % of total lipids in the liposomal formulations.

For example, liposomal formulations of leelamine, ATK or both leelamine and ATK include L-alpha-phosphatidylcholine (ePC) and 1,2-dipalmitoyl-sn-glycero-3-phosphoethanolamine-N-[methoxy(polyethylene glycol)-2000] (DPPE-PEG-2000) in a 95:5 mol % ratio according to aspects of the present invention.

According to aspects of the present invention, liposomal formulations of leelamine, ATK or both leelamine and ATK include at least one polyethylene glycol modified neutral lipid, wherein the total amount of polyethylene glycol modified neutral lipid is an amount in the range of 2.5-30 molar percent, inclusive, of total lipids in the liposomal formulations such as 5-20 molar percent, inclusive, of total lipids in the liposomal formulations and further including one or more anionic, cationic or neutral lipids in an amount in the range of 70-97.5, inclusive, molar percent of total lipids in the liposomal formulations.

In addition to containing leelamine, ATK or both leelamine and ATK, liposomes of the present invention optionally contain any of a variety of useful biologically active molecules and substances including, but not limited to, adjunct therapeutics, proteins, peptides, carbohydrates, oligosaccharides, drugs, and nucleic acids capable of being complexed with the liposomes. The term "biologically active molecules and substances" refers molecules or substances that exert a biological effect in vitro and/or in vivo, such as, but not limited to, nucleic acids, inhibitory RNA, siRNA, shRNA, ribozymes, antisense nucleic acids, antibodies, hormones, small molecules, aptamers, decoy molecules and toxins.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003; L. V. Allen, Jr. et al., Ansel's Pharmaceutical Dosage Forms and Drug Delivery Systems, 8th Ed., Philadelphia, Pa.: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

Liposomes including ATK are generated by methods which exclude exposure of the ATK to temperatures above room temperature to avoid a decrease in therapeutic efficacy of ATK according to aspects of the present invention.

In particular aspects, compositions of the present invention are formulated for topical application. In further particular aspects, compositions of the present invention are formulated for topical application and are characterized by less than 10% absorption of an active ingredient in the composition into the system of an individual treated topically. In still further particular aspects, compositions of the present invention are formulated for topical application and are characterized by less than 9%, 8%, 7%, 6%, 5%, 4%, 3%, 2%, 1% absorption of an active ingredient in the composition into the system of an individual treated topically. Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

Pharmaceutical compositions provided according to aspects of the present invention are suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

A topical formulation can be an ointment, lotion, cream or gel in particular aspects. Topical dosage forms such as ointment, lotion, cream or gel bases are described in Remington: The Science and Practice of Pharmacy, 21$^{st}$ Ed., Lippincott Williams & Wilkins, 2006, p. 880-882 and p. 886-888; and in Allen, L. V. et al., Ansel's Pharmaceutical Dosage Forms and Drug Delivery Systems, 8$^{th}$ Ed., Lippincott Williams & Wilkins, 2005, p. 277-297.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, one or more anti-cancer compounds described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to leelamine and/or ATK, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

Pharmaceutically acceptable carriers and formulation of pharmaceutical compositions are known in the art, illustratively including, but not limited to, as described in Remington: The Science and Practice of Pharmacy, 21$^{st}$ E a Lippincott, Williams & Wilkins, Philadelphia, Pa., 2006; and Allen, L. V. et al., Ansel's Pharmaceutical Dosage Forms and Drug Delivery Systems, 8$^{th}$ Ed., Lippincott, Williams & Wilkins, Philadelphia, Pa., 2005.

A "pharmaceutically acceptable" salt, ester, amide or solvate is suitable for use in a subject without undue toxicity or irritation to the subject and is effective for their intended use.

Pharmaceutically acceptable salts include pharmaceutically acceptable acid addition salts and base addition salts. Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N,N-dibenzylphenethylamine, 1-ephenamine, N,N'-dibenzylethylenediamine, ethanolamine, ethylamine, ethylenediamine, glucosamine, histidine, hydrabamine, isopropylamine, 1h-imidazole, lysine, methylamine, N-ethylpiperidine, N-methylpiperidine, N-methylmorpholine, N,N-dimethylaniline, piperazine, trolamine, methylglucamine, purines, piperidine, pyridine, theobromine, tetramethylammonium compounds, tetraethylammonium compounds, trimethylamine, triethylamine, tripropylamine and tributylamine and metal cations such as aluminum, calcium, copper, iron, lithium, magnesium, manganese, potassium, sodium, and zinc.

Pharmaceutically acceptable solvates illustratively include hydrates, ethanolates, methanolates.

Exemplary pharmaceutically acceptable amides include amides derived from ammonia, primary C1-C6 alkyl amines and secondary C1-C6 dialkyl amines including those in the form of a 5- or 6-member nitrogen-containing heterocycle.

Leelamine is optionally included as leelamine hydrochloride.

Compositions including leelamine and ATK according to aspects of the present invention have various utilities such as, but not limited to, utility in treatment of a subject having cancer or at risk of having cancer, such as skin cancer and other cancers including, but not limited to, cancers of the liver, prostate, breast, brain, stomach, pancreas, blood cells, uterus, cervix, ovary, lung, colon, connective tissues (sarcomas) and other soft tissues.

Compositions including leelamine and ATK according to aspects of the present invention have utility in treatment of a subject having skin cancer or at risk of having skin cancer, including basal cell carcinoma, squamous cell carcinoma and malignant melanoma.

Methods of Treatment

Methods for treatment and/or prevention of pathological conditions in a subject are provided including administration of leelamine and ATK according to aspects of the present invention.

Methods for treatment and/or prevention of pathological conditions in a subject are provided including administration of both leelamine and ATK show synergistic effects.

Methods for treatment and/or prevention of pathological conditions in a subject are provided including administration of both leelamine and ATK allow for reduced effective dosage and increased therapeutic index of leelamine and/or ATK.

According to aspects, combination therapies include: (1) administration of pharmaceutical compositions of the present invention that include leelamine and ATK in combination; (2) co-administration of leelamine and ATK wherein the leelamine and ATK are not formulated in the same composition. When using separate formulations, leelamine and ATK may be administered at the same time, or leelamine may be administered at intermittent times, staggered times, prior to, subsequent to, or combinations thereof, with reference to the administration of ATK.

Methods for treatment and/or prevention of pathological conditions in a subject are provided including administration of liposomal compositions including leelamine, liposomal compositions including ATK or liposomal compositions including both leelamine and ATK according to aspects of the present invention.

Particular cancers treated using methods and compositions described herein are characterized by abnormal cell proliferation including, but not limited to, pre-neoplastic hyperproliferation, cancer in-situ, neoplasms and metastasis. Methods and compositions of the present invention can be used for prophylaxis as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer.

A therapeutically effective amount of leelamine and ATK administered according to aspects of the present invention is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to an inventive composition, a therapeutically effective amount of a composition is effective to ameliorate or prevent one or more signs and/or symptoms of the condition. For example, a therapeutically effective amount of leelamine and ATK is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to an inventive composition.

Methods of treating a subject are provided according to aspects of the present invention which include administering a therapeutically effective amount of leelamine and ATK to a subject in need thereof, wherein the subject has an abnormal proliferative condition, such as cancer, pre-neoplastic hyperproliferation, cancer in-situ, neoplasms, metastasis, tumor or benign growth.

Subjects in need of treatment are identified as having, or at risk of having, cancer using well-known medical and diagnostic techniques.

The term "subject" refers to an individual in need of treatment for a pathological condition responsive to the beneficial effects of compositions of the present invention, particularly cancer. While the present invention describes compositions and methods for treatment of human subjects in need thereof, the present invention is not limited to human subjects and the term subject generally includes mammals and birds, such as, but not limited to, non-human primates, cats, dogs, cows, horses, rodents, pigs, sheep, goats and poultry.

Methods of treatment according to aspects of the present invention include administration of leelamine and ATK to a subject having skin cancer or at risk of having skin cancer, including basal cell carcinoma, squamous cell carcinoma and malignant melanoma.

Methods of treatment according to aspects of the present invention include administration of leelamine and ATK to a subject having cancer or at risk of having cancer, such as, but not limited to, cancers of the liver, prostate, breast, brain, stomach, pancreas, blood cells, uterus, cervix, ovary, lung, colon, connective tissues (sarcomas) and other soft tissues.

Methods of treatment of a subject having, or at risk of having, cancer, are provided according to aspects of the present invention including administration of a pharmaceutically effective amount of liposomes containing leelamine, liposomes containing ATK or liposomes containing both leelamine and ATK.

Liposomal formulations of anti-cancer compositions of the present invention are injected intravenously and/or applied topically according to aspects of the present invention.

Leelamine and ATK are administered to a subject by any of a variety of systemic and/or local routes according to aspects of methods of the present invention including, but not limited to, intravenous, intramuscular, subcutaneous, intraperitoneal, oral, otic, rectal, vaginal, topical, parenteral, pulmonary, ocular, nasal, intratumoral and mucosal.

Leelamine and ATK may be administered acutely or chronically according to aspects of methods of the present invention.

Leelamine and ATK may be administered: together in a single formulation; both separately; together or both separately as a unitary dose; or together or both separately in multiple doses. Leelamine and ATK may be administered together in a single formulation; both separately; together or both separately as a unitary dose; or together or both separately in multiple doses over a relatively limited period of time, such as seconds-hours. In a further embodiment, administration may include multiple doses of leelamine and ATK administered together in a single formulation, or separately, administered over a period of days-years, such as for chronic treatment of cancer.

A therapeutically effective amount of leelamine and ATK according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Combination Treatments

Combinations of therapeutic agents are administered according to aspects of the present invention. In some aspects, leelamine, ATK and at least one additional therapeutic agent are administered to a subject to treat cancer in a subject in need thereof. In still further aspects, leelamine, ATK and at least two additional therapeutic agents are administered to a subject to treat cancer in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Treatments including administration of both leelamine and ATK show synergistic effects. Combination therapies utilizing leelamine, ATK and one or more additional therapeutic agents may show further synergistic effects.

According to aspects of the present invention, combination therapies include: (1) administration of pharmaceutical compositions that include leelamine and ATK in combination with one or more additional therapeutic agents; (2) co-administration of leelamine and ATK with one or more additional therapeutic agents wherein none of leelamine, ATK and the one or more additional therapeutic agents are formulated in the same composition and (3) co-administration of leelamine and ATK with one or more additional therapeutic agents wherein leelamine and ATK are formulated in the same composition and wherein the one or more additional therapeutic agents have not been formulated in the same composition. When using separate formulations, leelamine, ATK and the one or more additional therapeutic agents may be administered at the same time or at different times; and two or more of leelamine, ATK and the one or more additional therapeutic agents may be administered at the same time or at different times with reference to the other therapeutic agents.

Combination treatments including leelamine and ATK with one or more additional therapeutic agents can allow for reduced effective dosage and increased therapeutic index of the compositions of the present invention and the one or more additional therapeutic agents used in methods of the present invention.

Optionally, a method of treating a subject having cancer or at risk of having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

Commercial Packages

Commercial packages are provided according to aspects of the present invention for treating cancer in a subject in need thereof, including leelamine and ATK; or a salt, stereoisomer, hydrate, amide or ester of leelamine and/or ATK. One or more auxiliary components are optionally included in commercial packages of the present invention, such as a pharmaceutically acceptable carrier exemplified by a buffer, diluent or a reconstituting agent.

A commercial package including a liposomal formulation of leelamine or a salt, stereoisomer, hydrate, amide or ester thereof, ATK or a salt, stereoisomer, hydrate, amide or ester thereof or leelamine and ATK, or a salt, stereoisomer, hydrate, amide or ester thereof; or a salt, stereoisomer, hydrate, amide or ester of either or both thereof.

Embodiments of inventive compositions and methods are illustrated in the following examples. These examples are provided for illustrative purposes and are not considered limitations on the scope of inventive compositions and methods.

Examples

Cell Lines and Culture Conditions

Human fibroblast FF2441 cells and metastatic melanoma cell lines UACC 903 and 1205 Lu were maintained in DMEM (Invitrogen), supplemented with 10% FBS (Hyclone). Cell lines were maintained in a 37° C. humidified 5% CO2 atmosphere incubator and periodically monitored for phenotypic and genotypic characteristics, and for tumorigenic potential.

Cell Viability Analysis

Viability of fibroblast and melanoma cells (UACC 903 and 1205 Lu) following treatment with ATK, leelamine, nanolipoATK, and nanolipoATK-999 was measured by MTS assay (Promega, Madison, Wis.). Briefly, $5 \times 10^3$ melanoma or fibroblast (FF2441) cells were plated per well in 100 μL of media and grown in 96-well plates for 48 hours. Cells were then treated with ATK alone, leelamine alone, nanolipoATK, nanolipoee, or nanoleelATK-999 for 24 hours before measuring cell viability.

Synergy Analysis when Treating Cultured Cells with ATK and Leelamine

UACC 903 cells were seeded into a 96-well plate at a density of $5 \times 10^3$ per well in 100 μL of media and grown for 48 hours. Cells were treated with 15-35 μmol/L of ATK (Sigma Chemical Co. St. Louis, Mo.) and 1.5 μmol/L, 2.5 μmol/L, or 3.5 μmol/L of leelamine (Sigma Chemical Co. St. Louis, Mo.) singly or in combination for 24 hours. The viability was measured by MTS assay (Promega, Madison, Wis.). MTS refers to 3-(4,5-dimethylthiazol-2-yl)-5-(3-carboxymethoxyphenyl)-2-(4-sulfophenyl)-2H-tetrazolium)

and assays using MTS to determine cell viability are well-known, see for example Barltrop, J. A. et al. (1991) Bioorg. Med. Chem. Lett. 1, 611-4. Potential synergy between the drugs was assessed using the Chou-Talalay method to estimate the combination index (CI) with Calcusyn software, see T-C Chou and P. Talalay, Trends Pharmacol. Sci. 4:450-454, 1983 and Chou T C, Talalay P., Adv Enzyme Regul 1984; 22:27-55. CI values of <0.9 were considered synergistic, >1.1 considered antagonistic, and values 0.9-1.1 considered as nearly additive.

Generation of Nanoliposomes

ATK alone or ATK plus leelamine at a 25:1 ratio were encapsulated into nanoliposomes called nanolipoATK and nanoleelATK-999, respectively. This was accomplished by combining L-α-phosphatidylcholine (ePC) and 1,2-dipalmitoyl-sn-glycero-3-phosphoethanolamine-N-[methoxy(polyethylene glycol)-2000]ammonium salt (DPPE-PEG-2000) in chloroform at 95:5 mol % for a final lipid concentration of 25 mg/mL (Avanti Polar Lipids Inc—Alabaster, Ala.). Solvent was removed and mixture dried under nitrogen gas followed by resuspension in sterile saline with vortexing every 5 minutes over a 20 minute period followed by extrusion at through a 100-nm polycarbonate membrane using Avanti Mini Extruder (Avanti Polar Lipids Inc— Alabaster, Ala.). The particle size and charge characteristics were measured using a Malvern Zetasizer (Malvern Instruments, UK).

Statistical Analysis $IC_{50}$ values were calculated using Prism 4.0 GraphPad Software. Calculsyn software was used to evaluate synergy.

Determination of Leelamine $IC_{50}$ Values Against Melanoma Cell Lines

The melanoma cell lines UACC 903 and 1205 Lu, and normal human fibroblast cells FF2441, were treated with 1 μM, 1.5 μM, 2 μM, 2.5 μM, 3 μM, 3.5 μM, 4 μM, 4.5 μM, or 5 μM leelamine in DMSO. Cells were maintained in DMEM supplemented with 10% FBS and L-glutamine. After 24 hours of treatment, an MTS assay was performed to determine the fractional cell viability relative to the DMSO control. $IC_{50}$ values were calculated using GraphPad Prism software. The efficacy of leelamine as an individual agent for inhibiting melanoma cell survival is demonstrated in FIG. 1 which shows a graph of viability of leelamine treated melanoma cells compared to cells treated with the DMSO control only as a function of the concentration of leelamine used. As shown in FIG. 1, leelamine treatment provides a dose-dependent decrease in viability of the melanoma cell lines UACC 903 and 1205 Lu, with half-maximal inhibitory concentrations ($IC_{50}$) of 2.8 µM and 3.8 µM, respectively. In contrast, leelamine did not kill the fibroblast cell line FF2441 cells at these concentrations.

Determination of ATK $IC_{50}$ Values Against Melanoma Cell Lines

Figure 2:
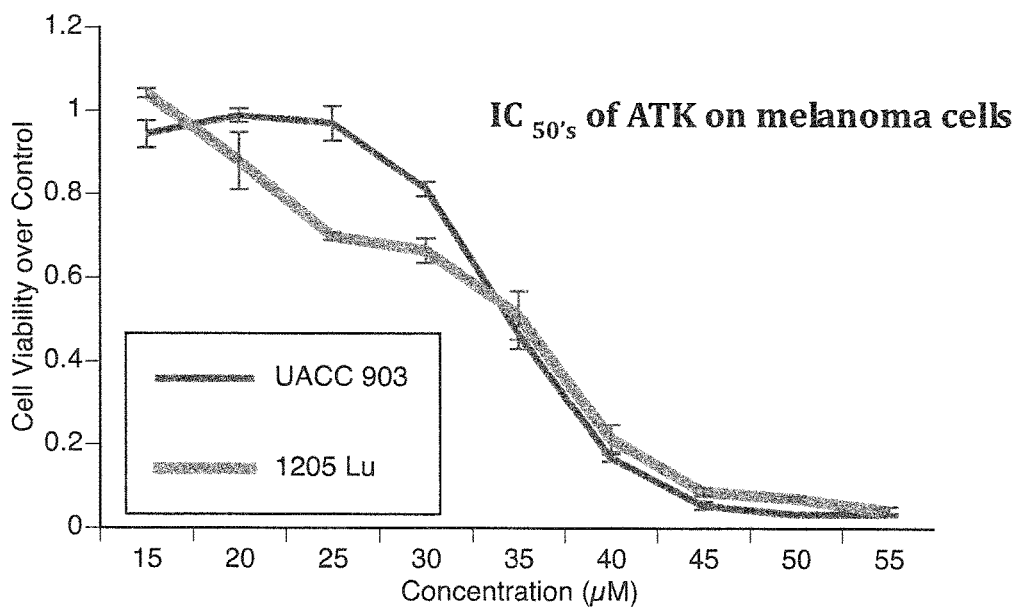
FIG. 2 is a graph showing ATK treatment provides a dose-dependent decrease in viability of the melanoma cell lines UACC 903 and 1205 Lu, with half-maximal inhibitory concentrations ($IC_{50}$) of ~35 µM.

The melanoma cell lines UACC 903 and 1205 Lu were treated with 15 µM, 20 µM, 25 µM, 30 µM, 35 µM, 40 µM, 45 µM, 50 µM, or 55 µM ATK in DMSO. Cells were maintained in DMEM supplemented with 10% FBS and L-glutamine. After 24 hours of treatment, an MTS assay was performed to determine the fractional cell viability relative to the DMSO control. $IC_{50}$ values were calculated using GraphPad Prism software. The activity of ATK as a single agent against UACC 903 and 1205 Lu cell lines is shown in FIG. 2, and in both cases the $IC_{50}$ value is ~35 µM.

Effect of Leelamine on UACC 903 Cell Viability

Figure 3:
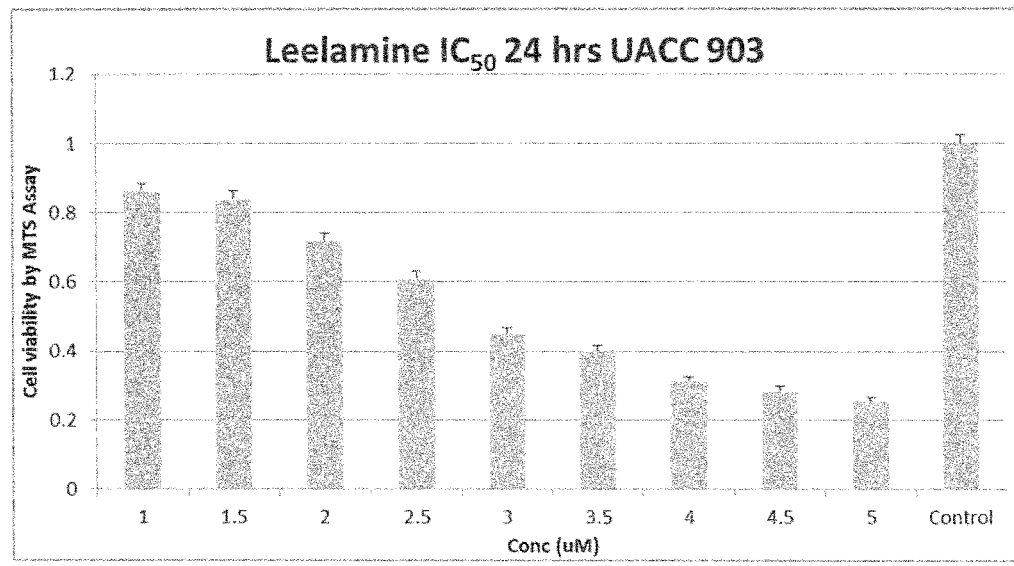
FIG. 3 is a graph showing the effect of leelamine on viability of UACC 903 melanoma cells.

UACC 903 cells were treated with 1 µM, 1.5 µM, 2 µM, 2.5 µM, 3 µM, 3.5 µM, 4 µM, 4.5 µM, or 5 µM leelamine or for 24 h prior to conducting an MTS assay to determine cell viability. Cells were maintained in DMEM supplemented with 10% FBS and L-glutamine. FIG. 3 is a graph showing the effect of leelamine on viability of UACC 903 melanoma cells.

Effect of ATK on UACC 903 Cell Viability

Figure 4:
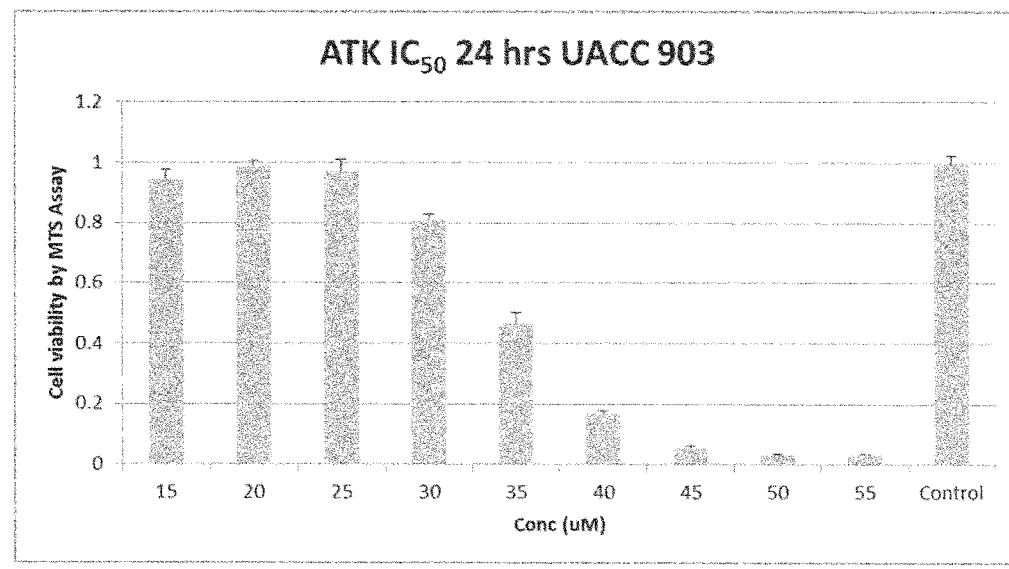
FIG. 4 is a graph showing the effect of ATK on viability of UACC 903 melanoma cells.

UACC 903 cells were treated with 15 µM, 20 µM, 25 µM, 30 µM, 35 µM, 40 µM, 45 µM, 50 µM, or 55 µM ATK for 24 h prior to conducting an MTS assay for cell viability. Cells were maintained in DMEM supplemented with 10% FBS and L-glutamine. The effect of leelamine and ATK treatment on UACC 903 cell viability is shown (FIG. 3 and FIG. 4, respectively). FIG. 4 is a graph showing the effect of ATK on viability of UACC 903 melanoma cells.

Effect of Treatment with Both ATK and Leelamine on UACC 903 Cell Viability—I

Figure 5:
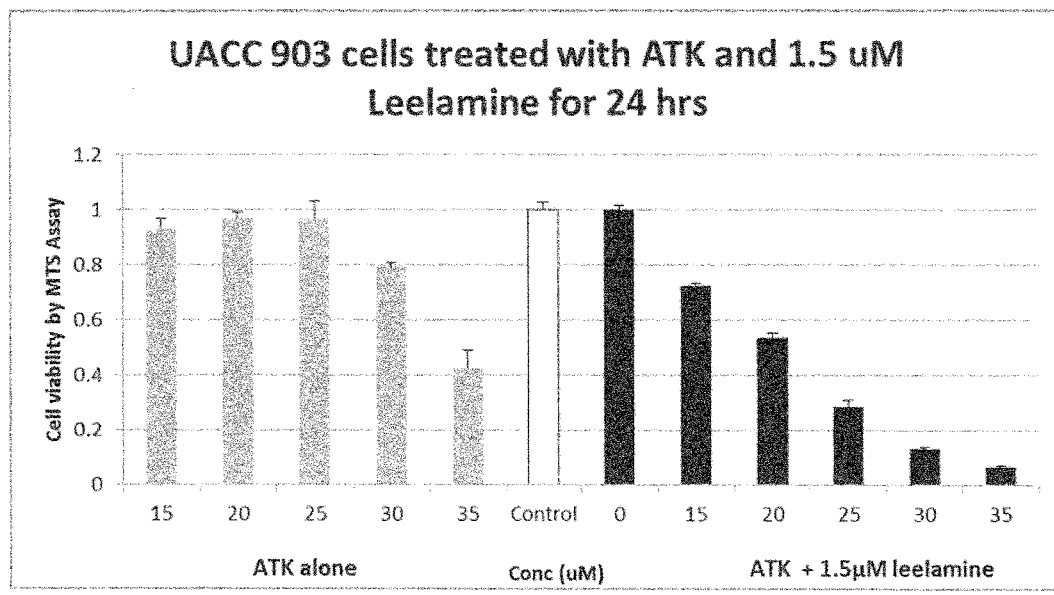
FIG. 5 is a graph showing the enhanced inhibitory effect of 1.5 µM leelamine and various concentrations of ATK in combination on viability of UACC 903 melanoma cells compared to ATK alone.

UACC 903 cells were treated with 15 µM, 20 µM, 25 µM, 30 µM or 35 µM ATK alone or a combination of 1.5 µM leelamine plus 15 µM, 20 µM, 25 µM, 30 µM or 35 µM ATK. Cells were maintained in DMEM supplemented with 10% FBS and L-glutamine. After 24 hours, an MTS assay was conducted to assay for cell viability relative to the DMSO control. FIG. 5 is a graph showing that when cells were treated with 1.5 µM leelamine and increasing concentrations of ATK in combination, an enhanced inhibitory effect was observed; grey bars=ATK alone; black bars=ATK+1.5 µM leelamine; white bar=DMSO control.

Figure 6:
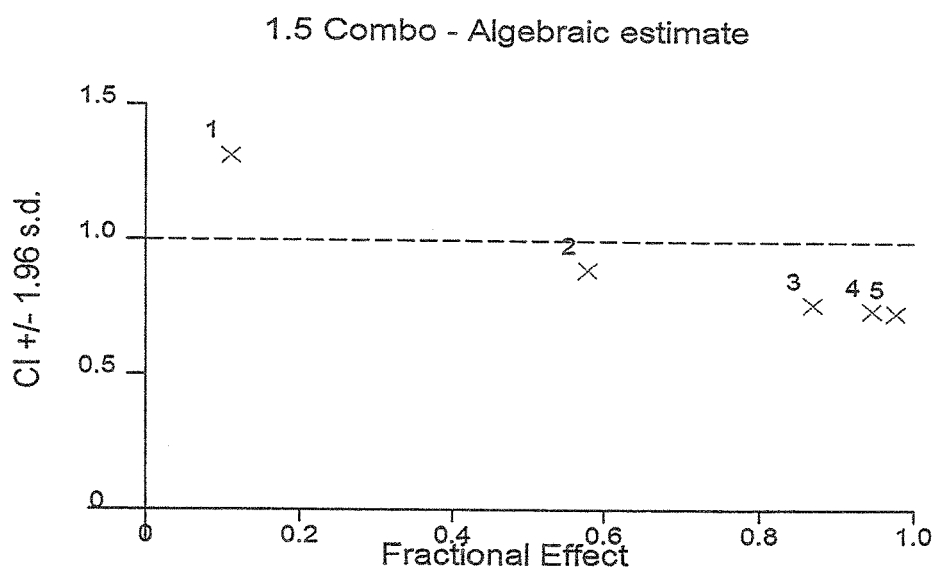
FIG. 6 is a graph showing CI Values demonstrating synergy of the effect of combinations of leelamine with ATK on viability of UACC 903 melanoma cells.

Combination index (CI) values were calculated and plotted using the Calcusyn software to determine synergy in trials where UACC 903 cells were treated with 15 µM, 20 µM, 25 µM, 30 µM or 35 µM ATK alone or a combination of 1.5 µM leelamine plus 15 µM, 20 µM, 25 µM, 30 µM or 35 µM ATK. CI values less than 0.8 are generally considered to be synergistic, as described in Chou, T. C., Drug combination studies and their synergy quantification using the Chou-Talalay method. Cancer research, 2010. 70(2): p. 440-6. FIG. 6 is a graph showing CI Values demonstrating synergy when combining 1.5 µM of leelamine with several concentrations of ATK in the range of 15 µM-35 µM. CI values are plotted with individual X's each indicating a different ATK:leelamine dose ratio: 1=1:0.1; 2=1:0.075; 3=1:0.06; 4=1:0.05; 5=1:0.043

Figure 7:
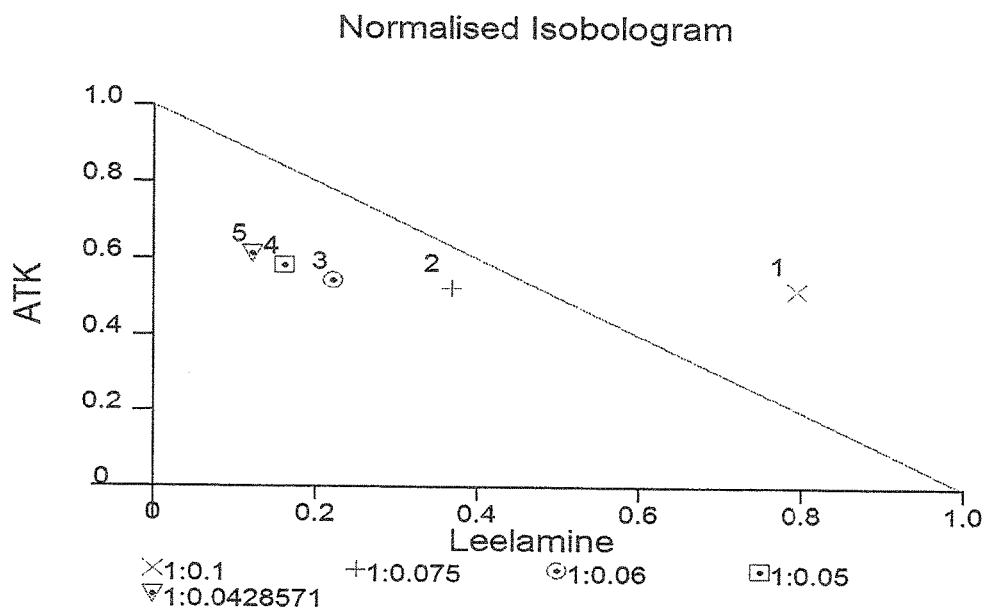
FIG. 7 is a normalized isoblogram, demonstrating synergy between leelamine and ATK.

A normalized isobologram is utilized as a standard measure of synergy in preclinical models as described in Zhao, L., M. G. Wientjes, and J. L. Au, Evaluation of combination chemotherapy: integration of nonlinear regression, curve shift, isobologram, and combination index analyses. Clinical cancer research: an official journal of the American Association for Cancer Research, 2004. 10(23): p. 7994-8004. Calcusyn software was used to generate a normalized isoblogram for trials where UACC 903 cells were treated with 15 µM, 20 µM, 25 µM, 30 µM or 35 µM ATK alone or a combination of 1.5 µM leelamine plus 15 µM, 20 µM, 25 µM, 30 µM or 35 µM ATK. FIG. 7 shows the normalized isoblogram, demonstrating synergy between 1.5 µM leelamine and ATK. Each point on the graph represents the indicated leelamine:ATK dose ratio, with synergistic combinations falling below the diagonal line.

Effect of Treatment with Both ATK and Leelamine on UACC 903 Cell Viability—II

Figure 8:
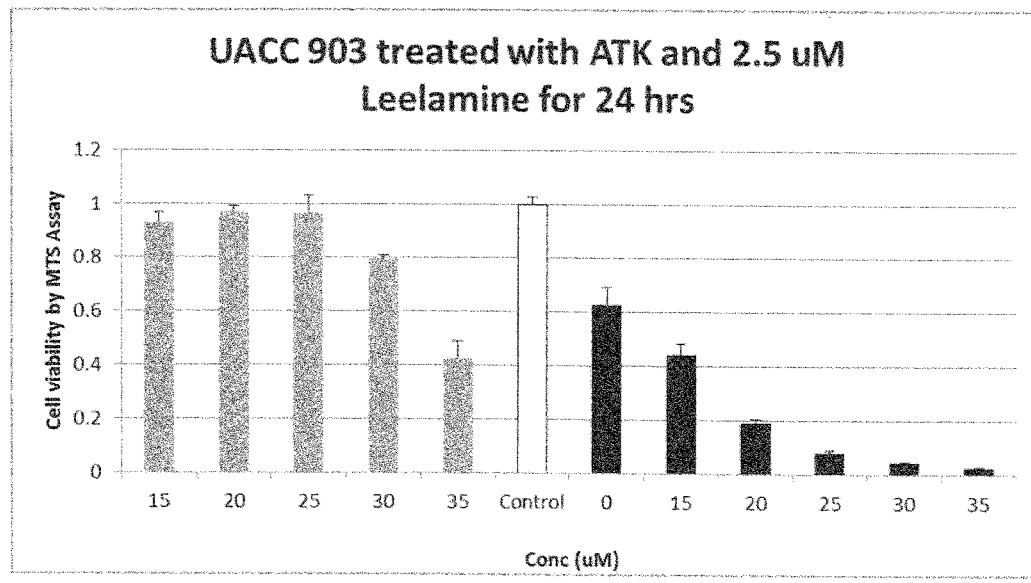
FIG. 8 is a graph showing the enhanced inhibitory effect of 2.5 µM leelamine and various concentrations of ATK in combination on viability of UACC 903 melanoma cells compared to ATK alone.

UACC 903 cells were treated with 15 µM, 20 µM, 25 µM, 30 µM or 35 µM ATK alone or a combination of 2.5 µM leelamine plus 15 µM, 20 µM, 25 µM, 30 µM or 35 µM ATK. Cells were maintained in DMEM supplemented with 10% FBS and L-glutamine. After 24 hours, an MTS assay was conducted to assay for cell viability relative to the DMSO control. FIG. 8 is a graph showing that when cells were treated with 2.5 µM leelamine and increasing concentrations of ATK in combination, an enhanced inhibitory effect was observed; grey bars=ATK alone; black bars=ATK+2.5 µM leelamine; what bar=DMSO control.

Figure 9:
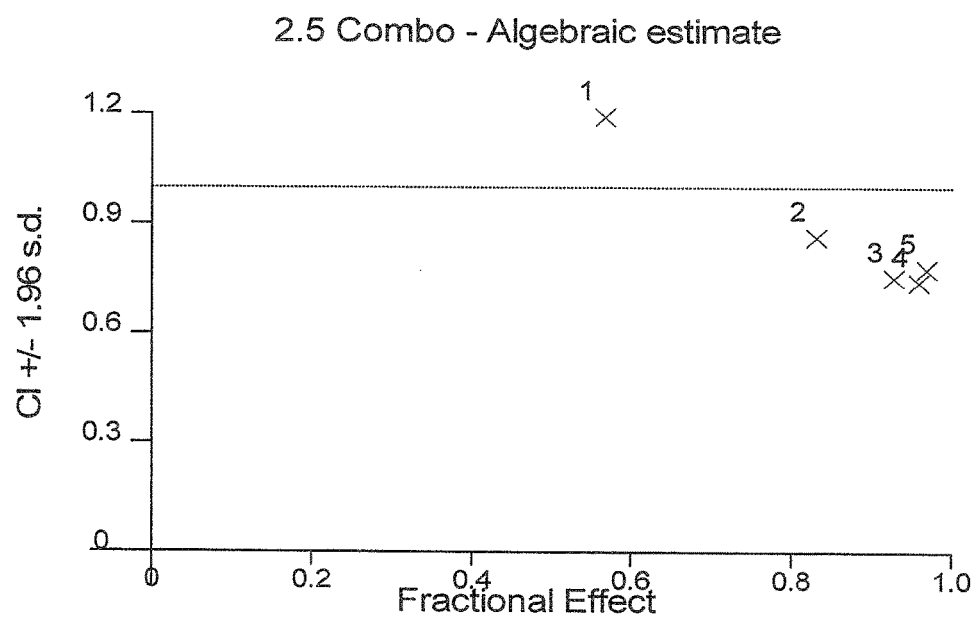
FIG. 9 is a graph showing CI Values demonstrating synergy of the effect of combinations of leelamine with ATK on viability of UACC 903 melanoma cells.

Combination index (CI) values were calculated and plotted using the Calcusyn software to determine synergy in trials where UACC 903 cells were treated with 15 µM, 20 µM, 25 µM, 30 µM or 35 µM ATK alone or a combination of 2.5 µM leelamine plus 15 µM, 20 µM, 25 µM, 30 µM or 35 µM ATK. FIG. 9 is a graph showing CI Values demonstrating synergy when combining 2.5 µM of leelamine with concentrations of ATK in the range of 15 µM-35 µM. CI values are plotted in FIG. 9 with individual X's each indicating a different ATK:leelamine dose ratio: 1=1:0.167; 2=1:0.125; 3=1:0.1; 4=1:0.083; 5=1:0.071. In all cases synergistic effects were observed for the indicated drug ratios.

Figure 10:
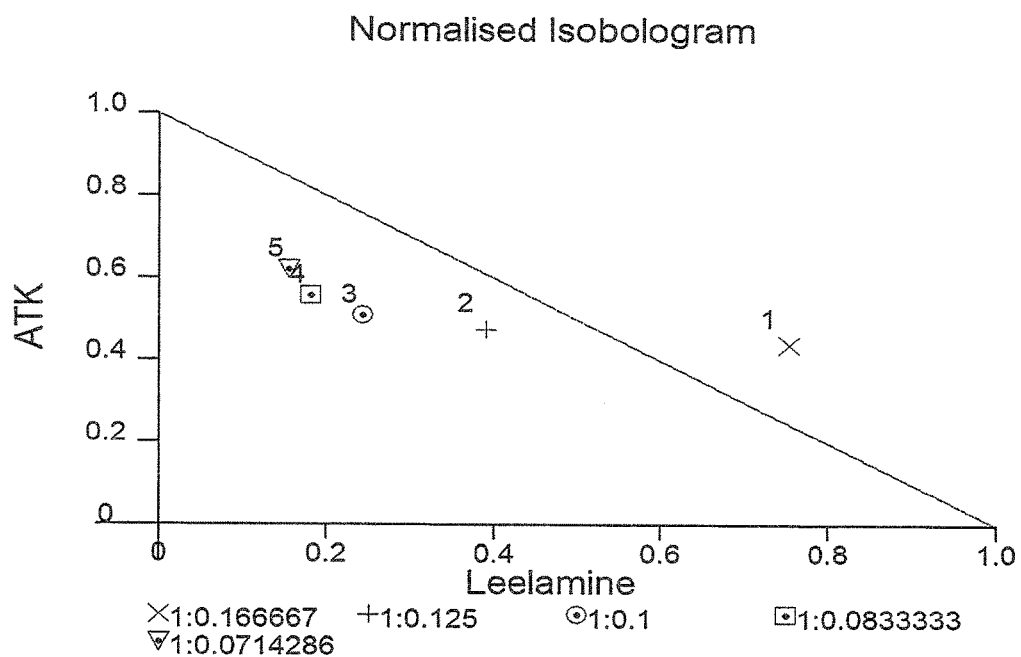
FIG. 10 is a normalized isoblogram, demonstrating synergy between leelamine and ATK.

Calcusyn software was used to generate a normalized isoblogram for trials where UACC 903 cells were treated with 15 µM, 20 µM, 25 µM, 30 µM or 35 µM ATK alone or a combination of 2.5 µM leelamine plus 15 µM, 20 µM, 25 µM, 30 µM or 35 µM ATK. FIG. 10 shows the normalized isoblogram, demonstrating synergy between 2.5 µM leelamine and ATK. Each point on the graph represents the indicated leelamine:ATK dose ratio, with synergistic combinations falling below the diagonal line.

Effect of Treatment with Both ATK and Leelamine on UACC 903 Cell Viability—III

Figure 11:
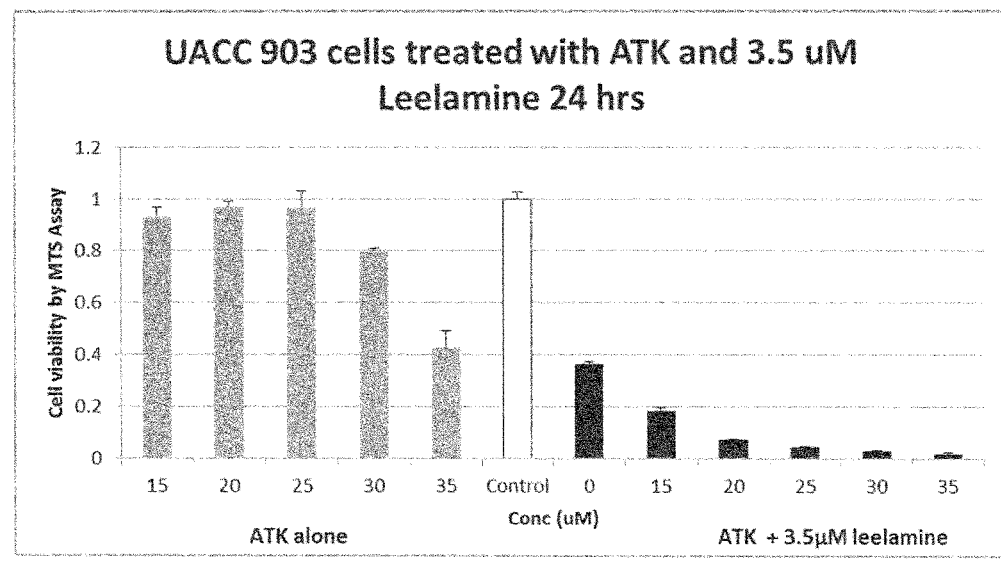
FIG. 11 is a graph showing the enhanced inhibitory effect of 3.5 µM leelamine and various concentrations of ATK in combination on viability of UACC 903 melanoma cells compared to ATK alone.

UACC 903 cells were treated with 15 µM, 20 µM, 25 µM, 30 µM or 35 µM ATK alone or a combination of 3.5 µM leelamine plus 15 µM, 20 µM, 25 µM, 30 µM or 35 µM ATK. Cells were maintained in DMEM supplemented with 10% FBS and L-glutamine. After 24 hours, an MTS assay was conducted to assay for cell viability relative to the DMSO control. FIG. 11 is a graph showing that when cells were treated with 3.5 µM leelamine and increasing concentrations of ATK in combination, an enhanced inhibitory effect was observed; grey bars=ATK alone; black bars=ATK+3.5 µM leelamine; white bar=DMSO control.

Figure 12:
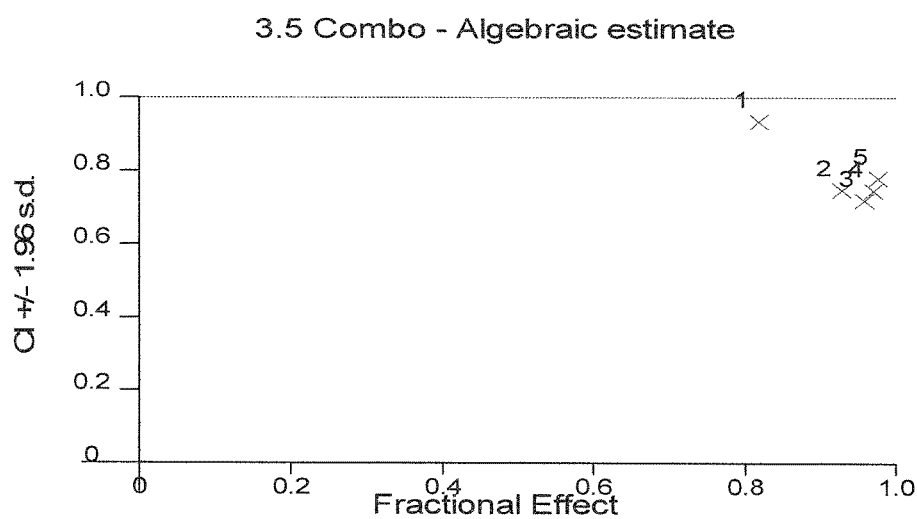
FIG. 12 is a graph showing CI Values demonstrating synergy of the effect of combinations of leelamine with ATK on viability of UACC 903 melanoma cells.

Combination index (CI) values were calculated and plotted using the Calcusyn software to determine synergy in trials where UACC 903 cells were treated with 15 µM, 20 µM, 25 µM, 30 µM or 35 µM ATK alone or a combination of 3.5 µM leelamine plus 15 µM, 20 µM, 25 µM, 30 µM or 35 µM ATK. FIG. 12 is a graph showing CI Values demonstrating synergy when combining 3.5 µM of Leelamine with concentrations of ATK in the range of 15 µM-35 µM.

CI values are plotted with individual X's each indicating a different ATK:leelamine dose ratio: 1=1:0.23; 2=1:0.175; 3=1:0.14; 4=1:0.12; 5=1:0.1.

Figure 13:
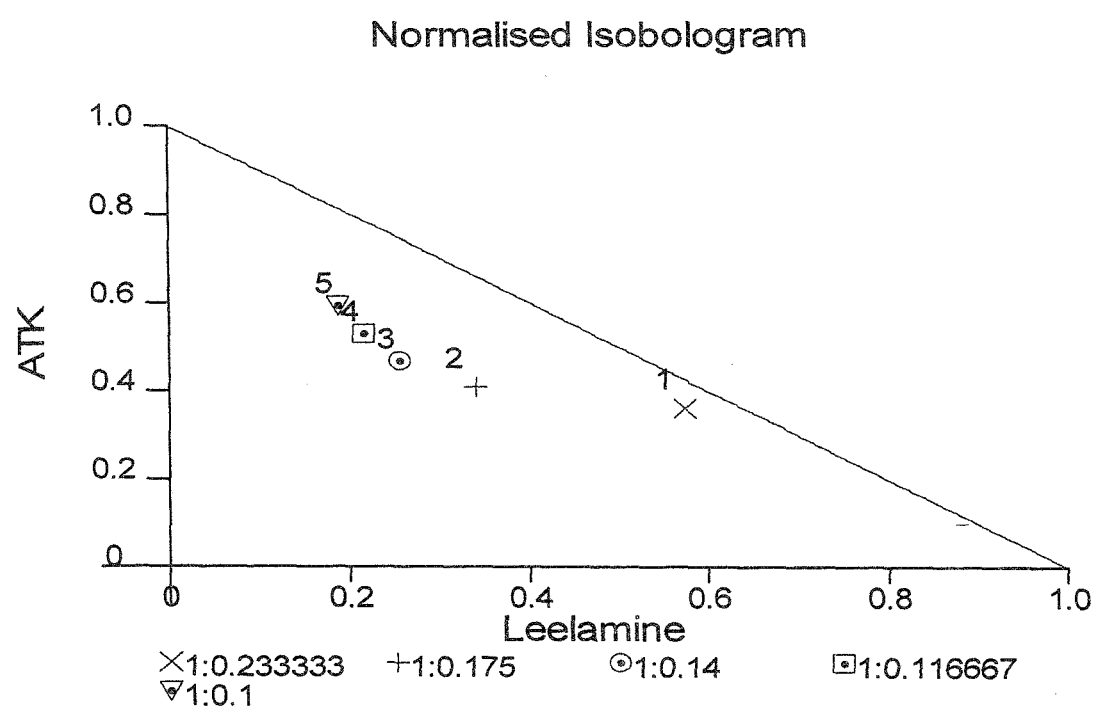
FIG. 13 is a normalized isoblogram, demonstrating synergy between leelamine and ATK.

Calcusyn software was used to generate a normalized isoblogram for trials where UACC 903 cells were treated with 15 μM, 20 μM, 25 μM, 30 μM or 35 μM ATK alone or a combination of 3.5 μM leelamine plus 15 μM, 20 μM, 25 μM, 30 μM or 35 μM ATK. FIG. 13 shows the normalized isoblogram, demonstrating synergy between 3.5 μM leelamine and ATK. Each point on the graph represents the indicated leelamine:ATK dose ratio, with synergistic combinations falling below the diagonal line.

UV/Vis absorbance for quantitation of free leelamine and ATK and for liposomal leelamine and liposomal ATK.

Figure 14A:
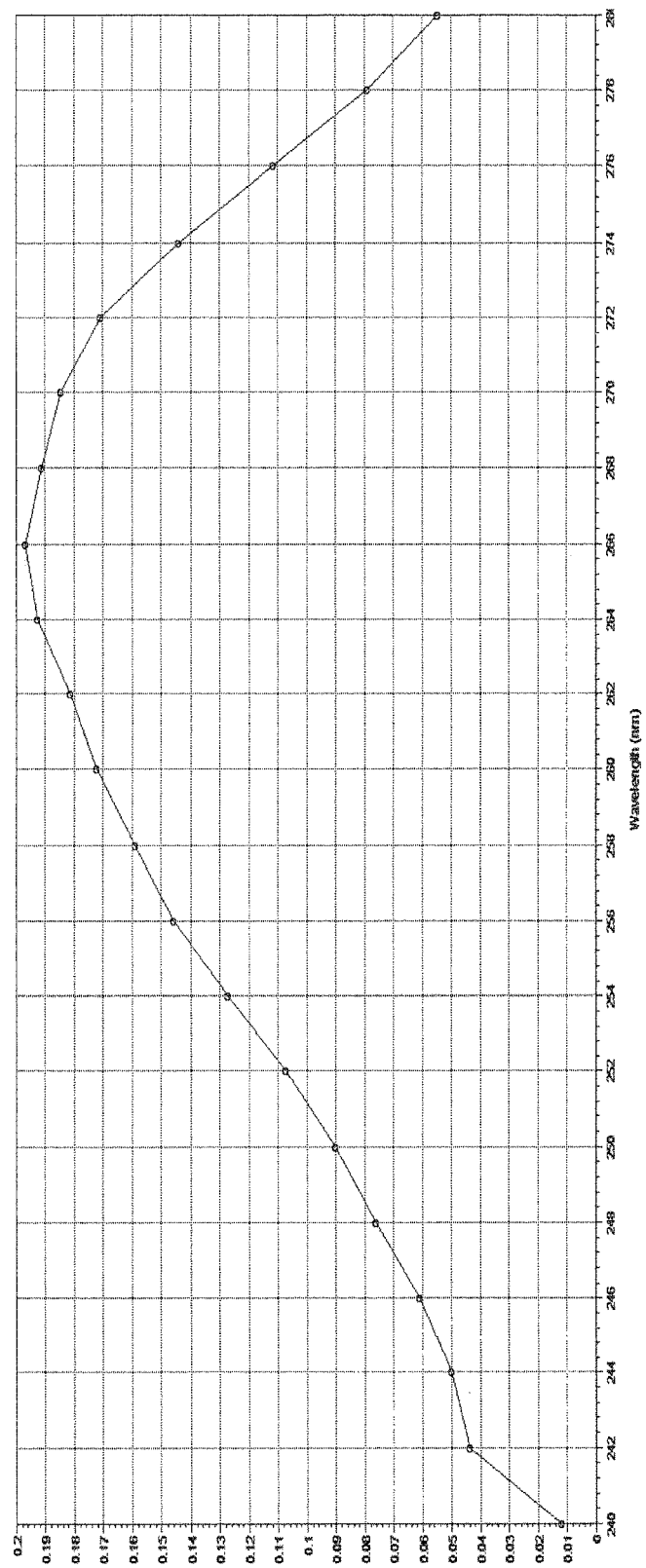
FIG. 14A is a graph showing the results of measurement of the UV/Vis absorbance spectrum of leelamine between 200 nm and 600 nm, indicating peak absorbance for leelamine at 266 nm.
Figure 14B:
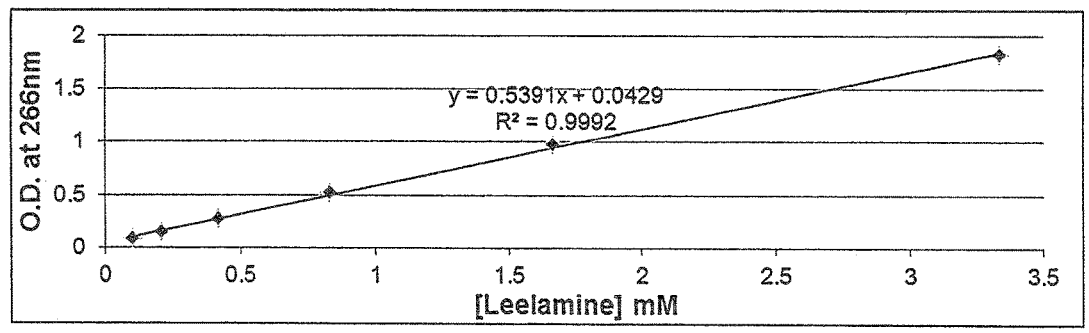
FIG. 14B is a standard curve for determining leelamine concentration generated at optical density (O.D.) 266 nm.

A Softmax Pro 5 spectrophotometer was used to measure the UV/Vis absorbance spectrum of leelamine between 200 nm and 600 nm. The peak absorbance for leelamine was shown to occur at 266 nm as shown in FIG. 14A. A standard curve for determining leelamine concentration was generated at this absorbance value as shown in FIG. 14B.

Figure 15A:
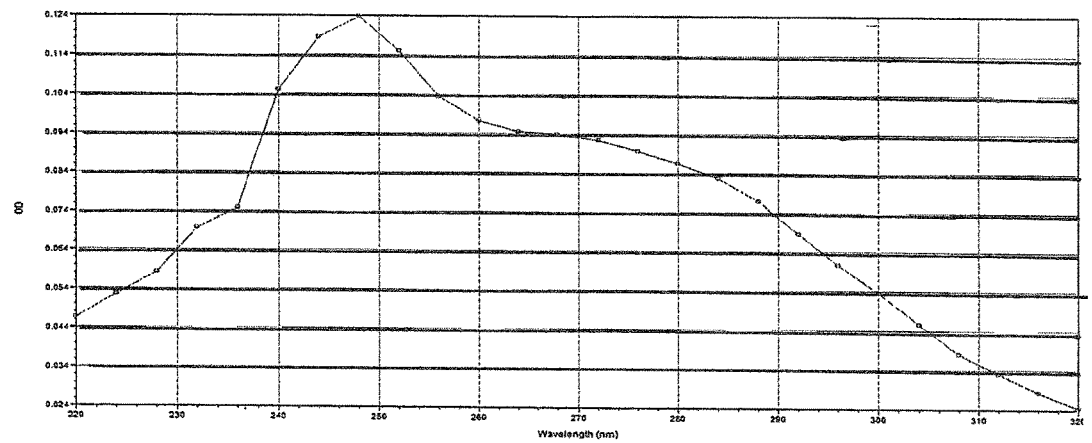
FIG. 15A is a graph showing the results of measurement of the UV/Vis absorbance spectrum of ATK between 200 nm and 600 nm, indicating peak absorbance for ATK at 248 nm.
Figure 15B:
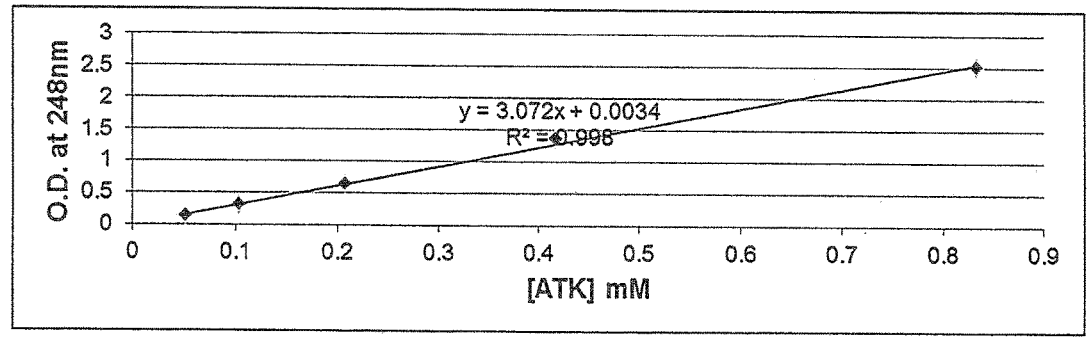
FIG. 15B is a standard curve for determining leelamine concentration generated at optical density (O.D.) 248 nm.

Similarly, a Softmax Pro 5 spectrophotometer was used to measure the UV/Vis absorbance spectrum of ATK between 200 nm and 600 nm. The peak absorbance for ATK was shown to occur at 248 nm as shown in FIG. 15A. A standard curve for determining ATK concentration was generated at this absorbance value as shown in FIG. 15B.

Figure 16A:
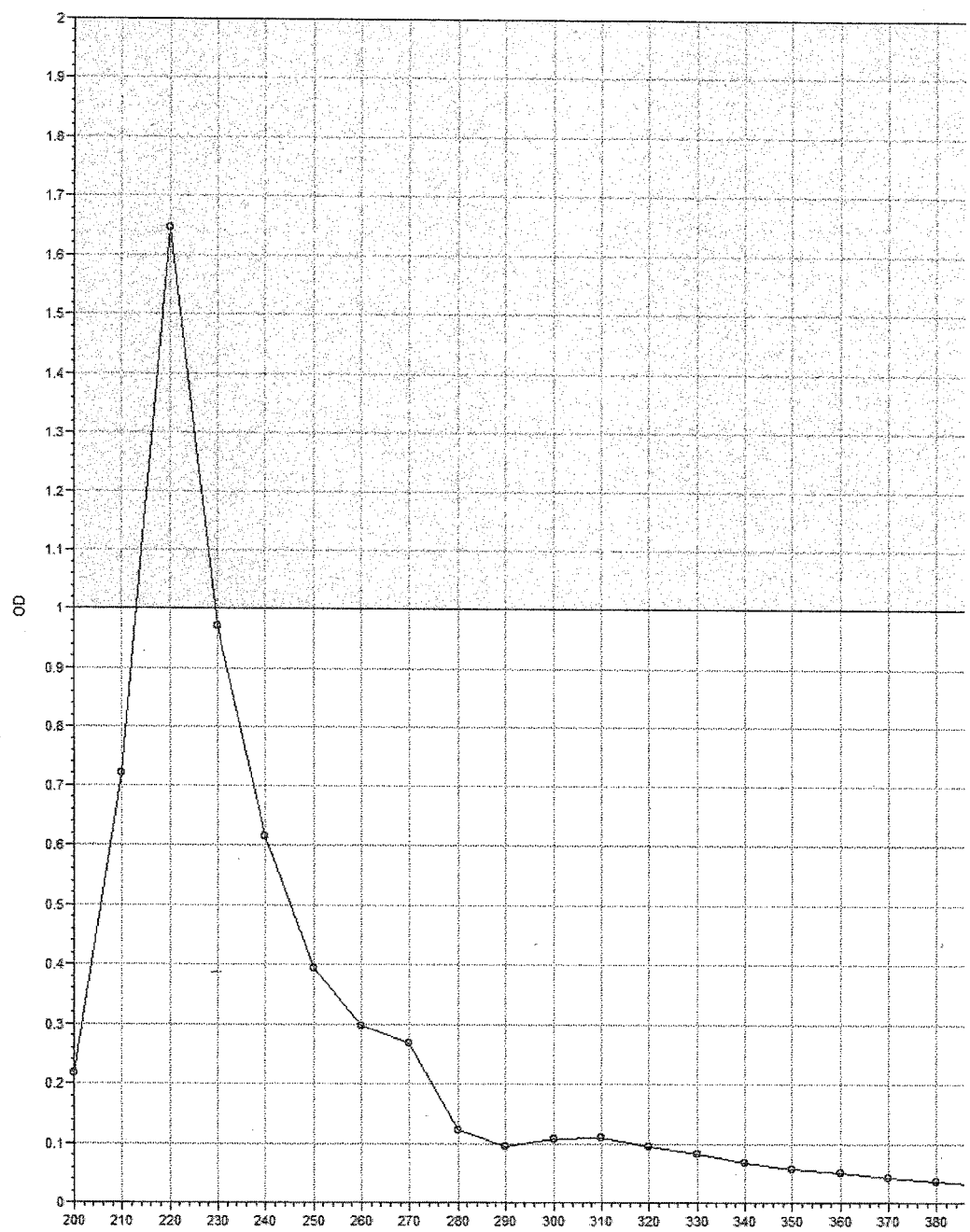
FIG. 16A is a graph showing the results of measurement of the UV/Vis absorbance spectrum of liposomal leelamine between 200 nm and 600 nm, indicating peak absorbance at 220 nm.
Figure 16B:
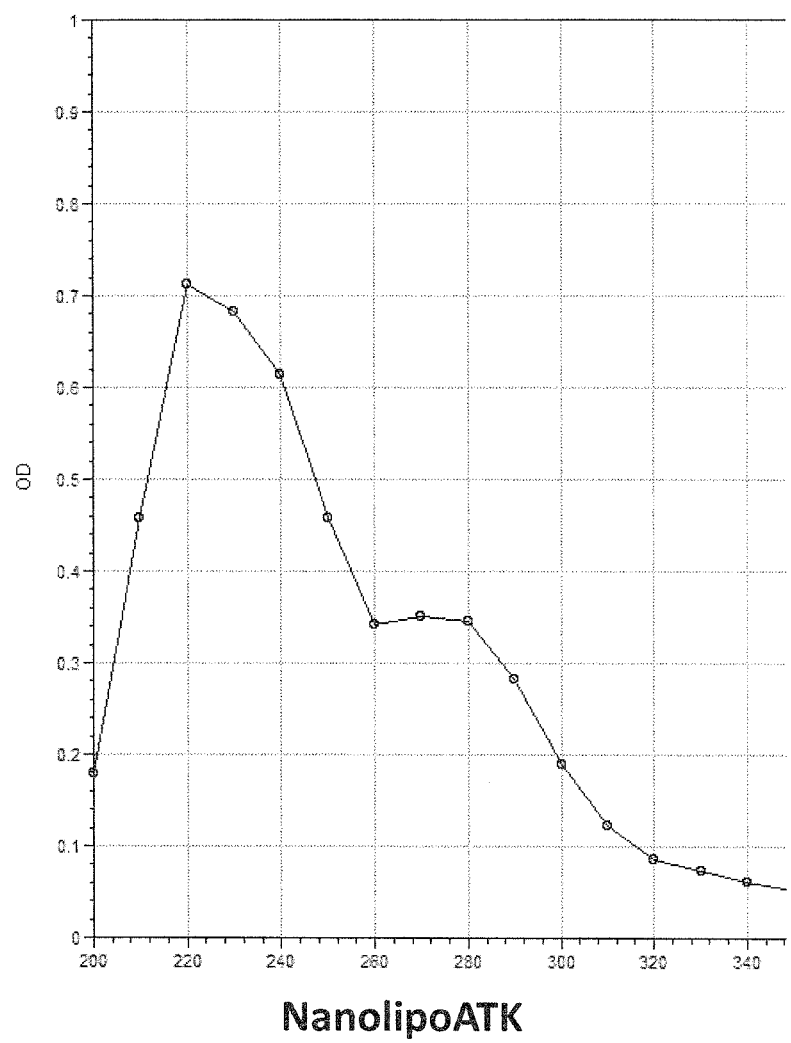
FIG. 16B is a graph showing the results of measurement of the UV/Vis absorbance spectrum of liposomal ATK between 200 nm and 600 nm, indicating peak absorbance at 220 nm.

A Softmax Pro 5 spectrophotometer was used to measure the UV/Vis absorbance spectrum of liposomal ATK (nanolipoATK) and liposomal leelamine (nanolipolee) between 200 nm and 600 nm. When leelamine and ATK are loaded into nanoliposomal particles, the peak absorbance of the liposome-associated drug is shifted to 220 nm as shown in FIGS. 16A and 16B, respectively. The difference in absorbance spectra between free drug and liposome-associated drug enables drug loading into nanoliposomes to be estimated via this method.

Treatment with Various Leelamine:ATK Dosing Ratios.

Figure 17:
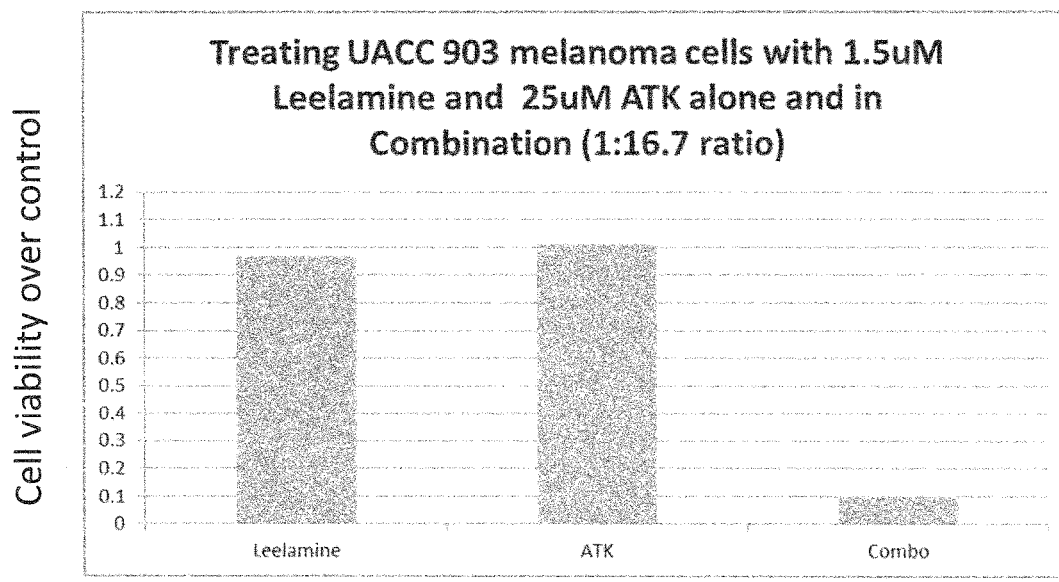
FIG. 17 is a graph showing results of treatment with leelamine alone, ATK alone, or leelamine and ATK ("Combo") in a 1:16.7 ratio, on UACC 903 melanoma cell viability.

UACC 903 melanoma cells were treated with 1.5 μM leelamine, 25 μM ATK or 1.5 μM leelamine plus 25 μM ATK. The combination of 1.5 μM leelamine and 25 μM ATK treatment is a 1:16.7 leelamine:ATK ratio. Cells were maintained in DMEM supplemented with 10% FBS and L-glutamine. After 24 hours, an MTS assay was conducted to assay for cell viability relative to the DMSO control. FIG. 17 is a graph showing results of treatment with 1.5 μM leelamine (bar labeled "Leelamine"), 25 μM ATK (bar labeled "ATK"), or 1.5 μM leelamine plus 25 μM ATK (bar labeled "Combo") on melanoma cell viability.

Figure 18:
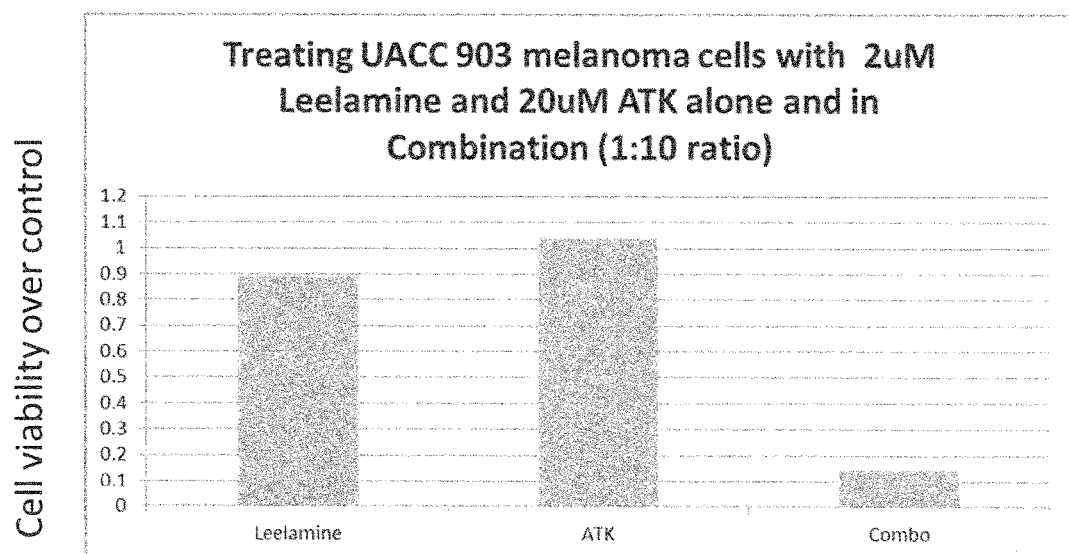
FIG. 18 is a graph showing results of treatment with leelamine alone, ATK alone, or leelamine and ATK ("Combo") in a 1:10 ratio, on UACC 903 melanoma cell viability.

UACC 903 melanoma cells were treated with 2 μM leelamine, 20 μM ATK or 2 μM leelamine plus 20 μM ATK. The combination of 2 μM leelamine and 20 μM ATK treatment is a 1:10 leelamine:ATK ratio. Cells were maintained in DMEM supplemented with 10% FBS and L-glutamine. After 24 hours, an MTS assay was conducted to assay for cell viability relative to the DMSO control. FIG. 18 is a graph showing results of treatment with 2 μM leelamine (bar labeled "Leelamine"), 20 μM ATK (bar labeled "ATK"), or 2 μM leelamine plus 20 μM ATK (bar labeled "Combo") on melanoma cell viability.

Figure 19:
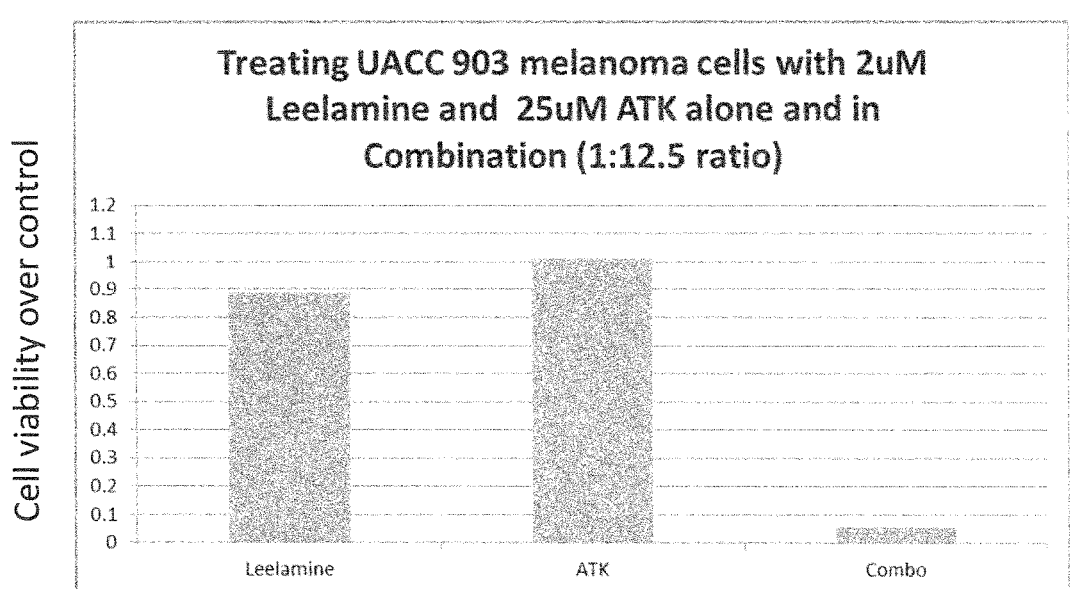
FIG. 19 is a graph showing results of treatment with leelamine alone, ATK alone, or leelamine and ATK ("Combo") in a 1:12.5 ratio, on UACC 903 melanoma cell viability.

UACC 903 melanoma cells were treated with 2 μM leelamine, 25 μM ATK or 2 μM leelamine plus 25 μM ATK. The combination of 2 μM leelamine and 25 μM ATK treatment is a 1:12.5 leelamine:ATK ratio. Cells were maintained in DMEM supplemented with 10% FBS and L-glutamine. After 24 hours, an MTS assay was conducted to assay for cell viability relative to the DMSO control. FIG. 19 is a graph showing results of treatment with 2 μM leelamine (bar labeled "Leelamine"), 25 μM ATK (bar labeled "ATK"), or 2 μM leelamine plus 25 μM ATK (bar labeled "Combo") on melanoma cell viability.

Figure 20:
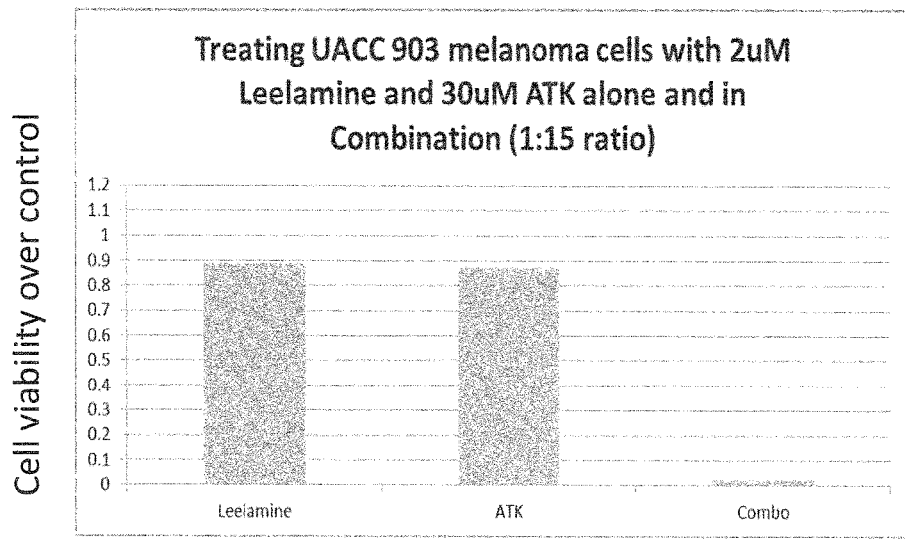
FIG. 20 is a graph showing results of treatment with leelamine alone, ATK alone, or leelamine and ATK ("Combo") in a 1:15 ratio, on UACC 903 melanoma cell viability.

UACC 903 melanoma cells were treated with 2 μM leelamine, 30 μM ATK or 2 μM leelamine plus 30 μM ATK. The combination of 2 μM leelamine and 30 μM ATK treatment is a 1:15 leelamine:ATK ratio. Cells were maintained in DMEM supplemented with 10% FBS and L-glutamine. After 24 hours, an MTS assay was conducted to assay for cell viability relative to the DMSO control. FIG. 20 is a graph showing results of treatment with 2 μM leelamine (bar labeled "Leelamine"), 30 μM ATK (bar labeled "ATK"), or 2 μM leelamine plus 30 μM ATK (bar labeled "Combo") on melanoma cell viability.

Figure 21:
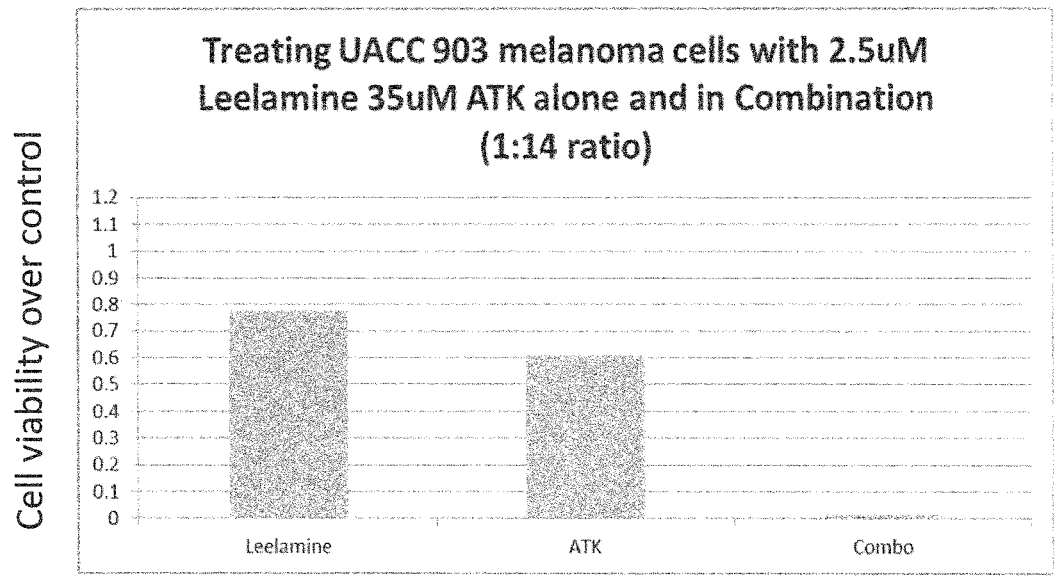
FIG. 21 is a graph showing results of treatment with leelamine alone, ATK alone, or leelamine and ATK ("Combo") in a 1:14 ratio, on UACC 903 melanoma cell viability.

UACC 903 melanoma cells were treated with 2.5 μM leelamine, 35 μM ATK or 2.5 μM leelamine plus 35 μM ATK. The combination of 2.5 μM leelamine and 35 μM ATK treatment is a 1:14 leelamine:ATK ratio. Cells were maintained in DMEM supplemented with 10% FBS and L-glutamine. After 24 hours, an MTS assay was conducted to assay for cell viability relative to the DMSO control. FIG. 21 is a graph showing results of treatment with 2.5 μM leelamine (bar labeled "Leelamine"), 35 μM ATK (bar labeled "ATK"), or 2.5 μM leelamine plus 35 μM ATK (bar labeled "Combo") on melanoma cell viability.

All leelamine:ATK dosing ratios in the range of 1:10-1:20 resulted in synergistic inhibition of melanoma cell growth and more than 80% inhibition of growth. Combination of leelamine and ATK at doses in the range of 1:12.5-1:20 led to nearly complete inhibition of growth, >90%. After evaluating different leelamine:ATK dosing ratios, it was determined that the optimal ratio for synergistic inhibition of melanoma cell growth was between 1:12.5 and 1:20.

Nanoliposome Formulation of ATK.

In this example, a nanoliposome formulation of ATK includes egg phosphatidylcholine (PC) and 1,2-dipalmitoryl-sn-glycero-3-phosphoethanolamine (DPPE) conjugatged polyethylene glycol (+PEG).

To prepare the nanoliposome formulation of this example, lipid stocks stored in a −20° C. freezer are retrieved and allowed to come to room temperature. A glass cuvette is used to prepare the lipid solution and ATK drug in ethanol by first adding 20 mg of egg phosphatidylcholine (PC) and 5 mg of 1,2-dipalmitoryl-sn-glycero-3-phosphoethanolamine (DPPE) conjugatged polyethylene glycol (+PEG) and then adding ATK such that the final concentration of ATK in the nanoliposomal formulation is 10 mM (1 mL final volume). Nitrogen gas is then passed over the material in the glass cuvette to evaporate chloroform and ethanol for at least 1 hour or until lipid is completely dry. Once the mixture is completely dry, 1 mL of solvent, in this case sterile water, is added and the resulting material is kept at room temperature. The top of the cuvette is covered and the material is mixed using a vortex mixer for 30 seconds on low setting every 15 minutes, at least 5 times. When the solution appears homogenous, it is sonicated in a room temperature water bath until the solution is transparent, a process that typically takes less than 5 minutes if the material has been sonicated properly. The resulting liposomal mixture is then extruded through a 100 μm filter 11 times. The resulting liposomal formulation of ATK is transferred into a 1.5 mL falcon tube for long-term storage at 4° C. The preparation of nanolipoATK was carried out entirely at room temperature because ATK is not heat stable.

Figure 22:
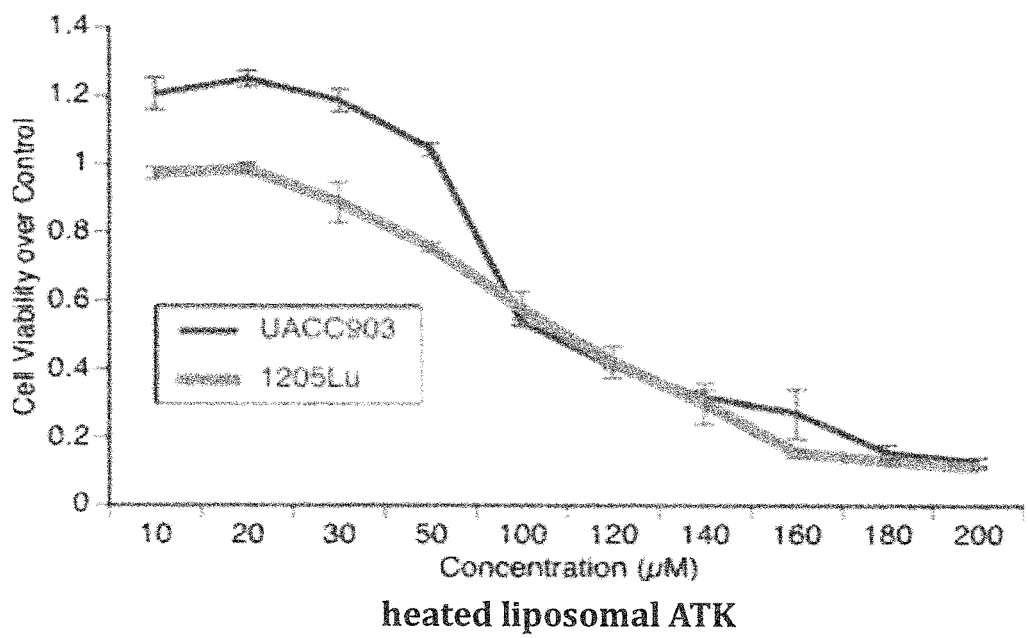
FIG. 22 is a graph showing the results of evaluation of the efficacy of liposomal ATK (nanolipoATK) on melanoma cell viability after heating at 70° C. and indicating that the efficacy of the heat-treated nanolipoATK particle decreased considerably to an $IC_{50}$ of 100 µM.

Heating at 70° C. During Preparation of nanolipoATK Decreases Effectiveness of ATK to Inhibit Melanoma Cells The melanoma cell lines UACC 903 and 1205 Lu were treated with different concentrations of nanolipoATK (10 μM-200 μM). NanolipoATK was heated for 1 hour during preparation of the nanoliposome. After 24 hours of treatment, an MTS assay was performed to determine the fractional cell viability relative to the DMSO control. Cells were maintained in DMEM supplemented with 10% FBS and L-glutamine. FIG. 22 is a graph showing the results of evaluation of the efficacy of liposomal ATK (nanolipoATK) on melanoma cell viability after heating at 70° C. When heated, the efficacy of the nanolipoATK particle decreased considerably to an $IC_{50}$ of 100 μM as shown in FIG. 22.

Figure 23:
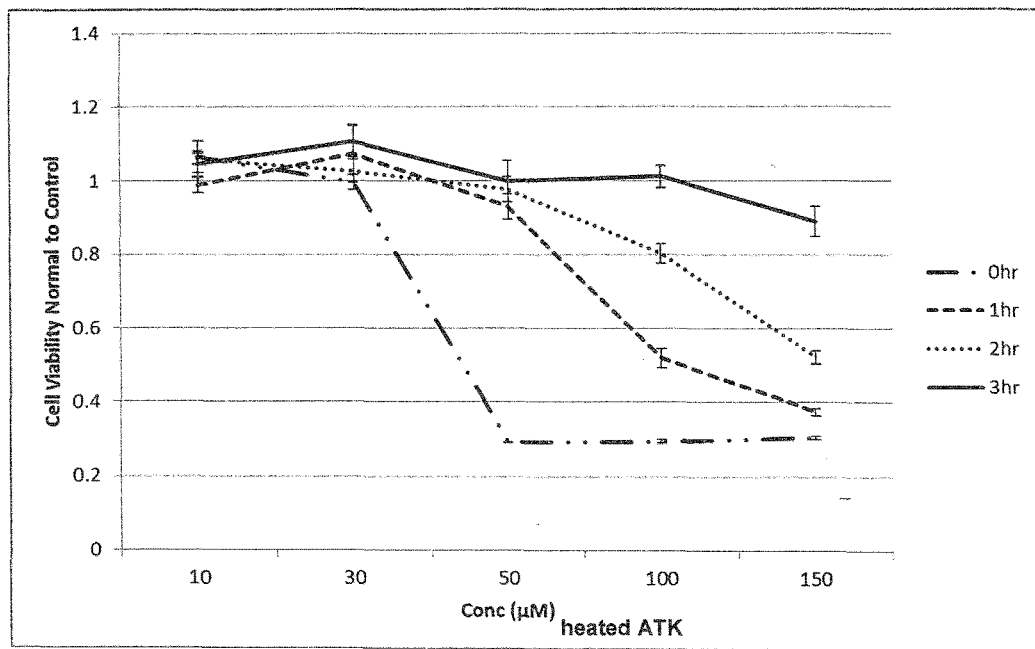
FIG. 23 is a graph showing activity of various concentrations of non-liposomal ATK against UACC 903 melanoma cells after exposure to 70° C. for 0, 1, 2, or 3 hours.

"Naked" ATK, also called "free" ATK herein, was heated at 70° C. during for 0, 1, 2 or 3 hours. "Naked" ATK is ATK in a non-liposomal carrier, here DMSO. UACC 903 cells were then treated with "naked" ATK heated at 70° C. for 1, 2 or 3 hours at concentrations in the range of 10 μM-150 μM. Unheated ATK (0 hours heat treatment at 70° C.) was administered to UACC 903 cells at concentrations in the range of 10 μM-150 μM for comparison. Cells were maintained in DMEM supplemented with 10% FBS and L-glutamine. After 24 hours of treatment, an MTS assay was performed to determine the fractional cell viability relative to the DMSO control. It was determined that heating "naked" ATK at 70° C. for 1 hour or more led to a substantial reduction in its inhibitory activity against melanoma cells as shown in FIG. 23. FIG. 23 is a graph of activity of non-liposomal ATK against UACC 903 melanoma cells after exposure at 70° C. for varying time periods.

Figure 24:
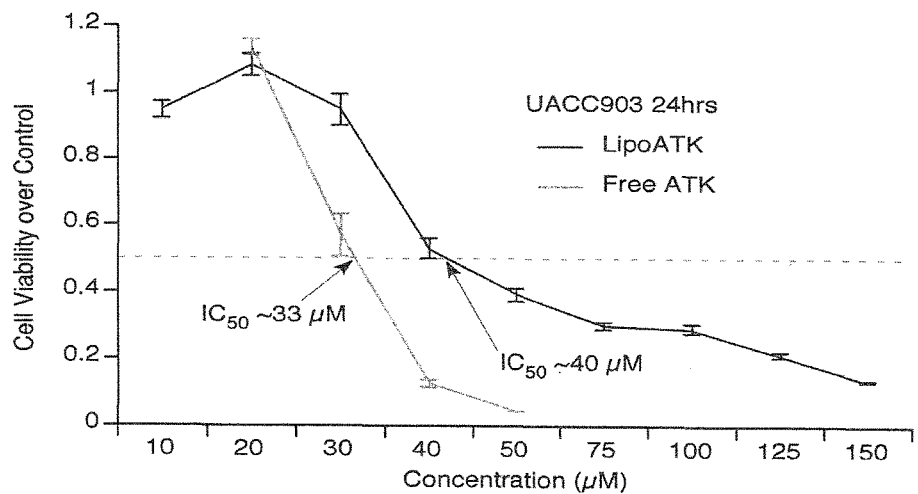
FIG. 24 is a graph showing efficacy of liposomal ATK (nanolipoATK) prepared at room temperature.

Efficacy of the nanolipoATK particle was restored to an $IC_{50}$ of ~40 μM when the procedure was conducted entirely at room temperature. UACC 903 cells were treated with different concentrations of nanolipoATK (10 μM-150 μM) and ATK in DMSO (10 μM-50 μM). NanolipoATK was kept at room temperature during preparation of the nanoliposome. Cells were maintained in DMEM supplemented with 10% FBS and L-glutamine. After 24 hours of treatment, an MTS assay was performed to determine the fractional cell viability relative to the DMSO control. $IC_{50}$ values were calculated using Graphpad Prism software. FIG. 24 is a graph showing efficacy of nanolipoATK prepared at room temperature.

Figure 25:
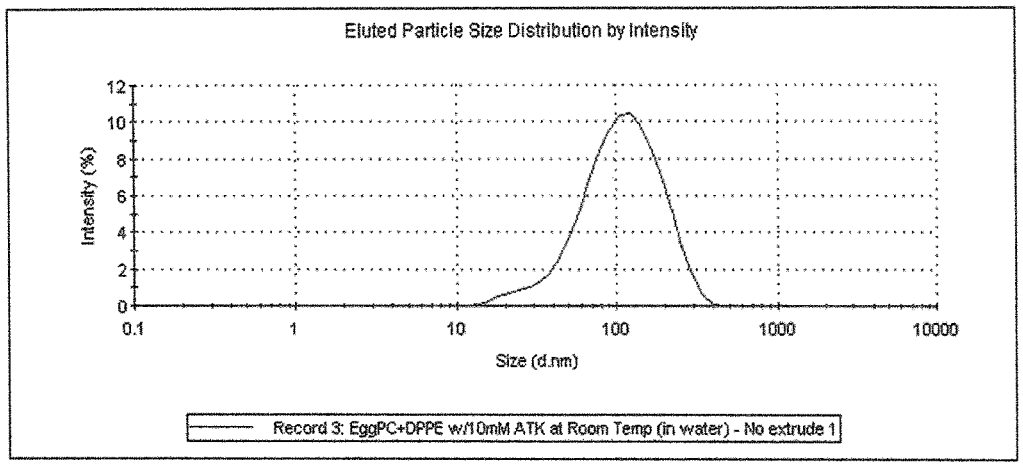
FIG. 25 is a graph showing the eluted particle size distribution by intensity of nanoliposomes prepared at room temperature containing ATK.

A Malvern Zetasizer was used to determine the range nanolipoATK particle sizes and to determine the mean nanolipoATK particle size. The mean size of the nanolipoATK particles was determined to be 120.6 nm, which is within the range considered to be therapeutic for nanoliposomes. FIG. 25 is a graph showing the eluted particle size distribution by intensity of nanoliposomes prepared at room temperature containing ATK.

Figure 26:
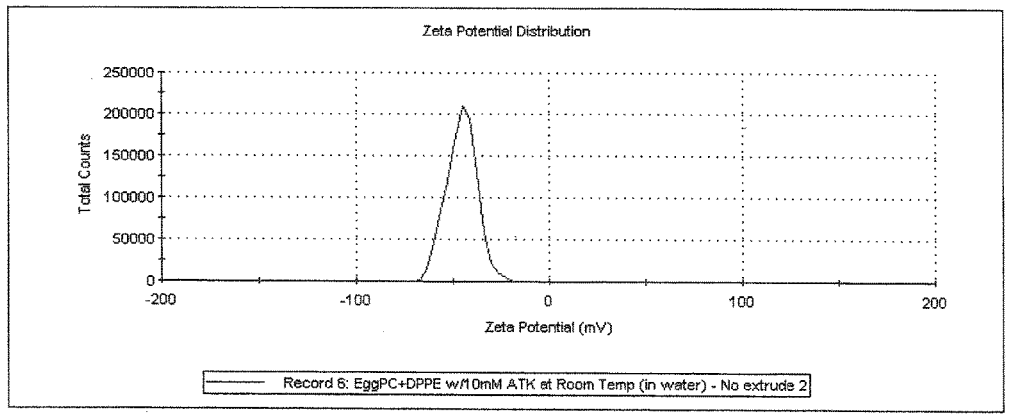
FIG. 26 is a graph showing zeta potential distribution of nanoliposomes prepared at room temperature containing ATK.

A Malvern Zetasizer was used to determine the range of nanoliposomal ATK zeta potentials and the mean nanolipoATK zeta potential. The nanolipoATK particles carried a small negative charge, −45.6 mV, which is also considered to be within the safe range for nanoliposomal therapy. FIG. 26 is a graph showing zeta potential distribution of nanoliposomes prepared at room temperature containing ATK. The distribution of all particle charges is shown, with a mean of −45.6 mV.

Figure 27:
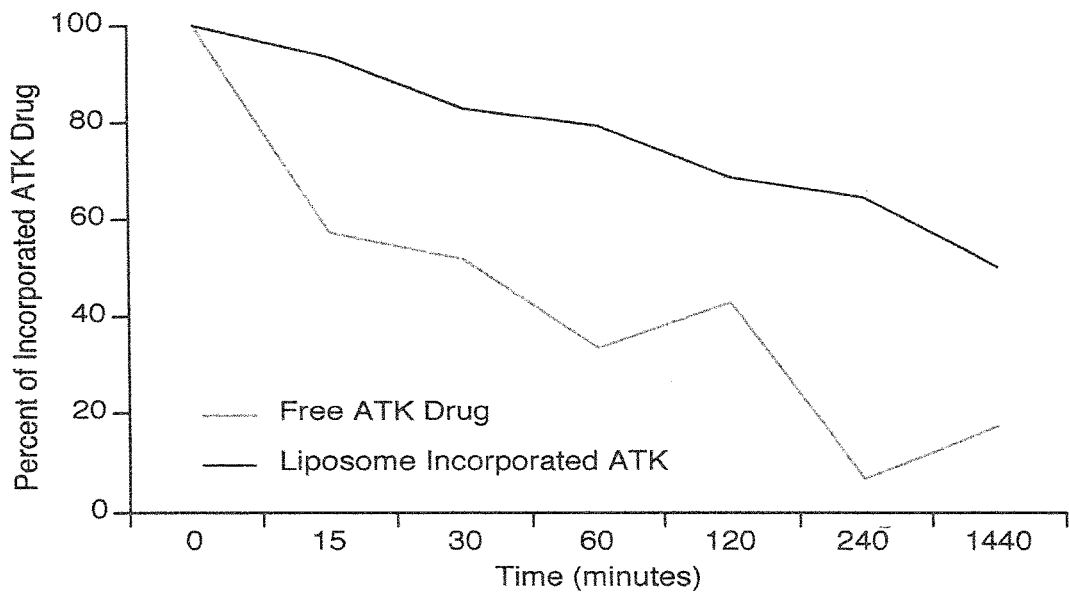
FIG. 27 is a graph showing removal of free unincorporated ATK from liposomal formulation prepared at 70° C. for 1 hour.

Purification of nanolipoATK by dialysis. FIG. 27 is a graph showing removal of free unincorporated ATK from liposomal formulation prepared at 70° C. for 1 hour. NanolipoATK was dialyzed against 0.9% saline for different periods of time in order to remove unincorporated ATK from the solution. Greater than 90% of free ATK was removed from the nanoliposomal mixture via this method, with a concomitant ~40% loss of nanolipoATK.

In this example, a nanoliposome formulation of leelamine includes egg phosphatidylcholine (PC) and 1,2-Dipalmitoryl-sn-Glycero-3-Phosphoethanolamine (DPPE) conjugatged polyethylene glycol (+PEG). To prepare the nanoliposome formulation of this example, lipid stocks stored in a −20° C. freezer are retrieved and allowed to come to room temperature. A glass cuvette is used to prepare the lipid solution and leelamine drug in ethanol by first adding 20 mg of egg phosphatidylcholine (PC) and 5 mg of 1,2-dipalmitoryl-sn-glycero-3-phosphoethanolamine (DPPE) conjugatged polyethylene glycol (+PEG) and then adding leelamine such that the final concentration of leelamine in the nanoliposomal formulation is 0.7 mM (1 mL final volume). Nitrogen gas is then passed over the material in the glass cuvette to evaporate chloroform and ethanol for at least 1 hour or until lipid is completely dry. Once the mixture is completely dry, 1 mL of solvent, in this case sterile water, is added and the resulting material is kept at room temperature. The top of the cuvette is covered and the material is mixed using a vortex mixer for 30 seconds on low setting every 15 minutes, at least 5 times. When the solution appears homogenous, it is sonicated in a room temperature water bath until the solution is transparent, a process that typically takes less than 5 minutes if the material has been sonicated properly. The resulting liposomal mixture is then extruded through a 100 μm filter 11 times. The resulting liposomal formulation of ATK is transferred into a 1.5 mL falcon tube for long-term storage at 4° C. In this example, the preparation of nanoliposomal leelamine (nanolipolee) was carried out entirely at room temperature.

Figure 28:
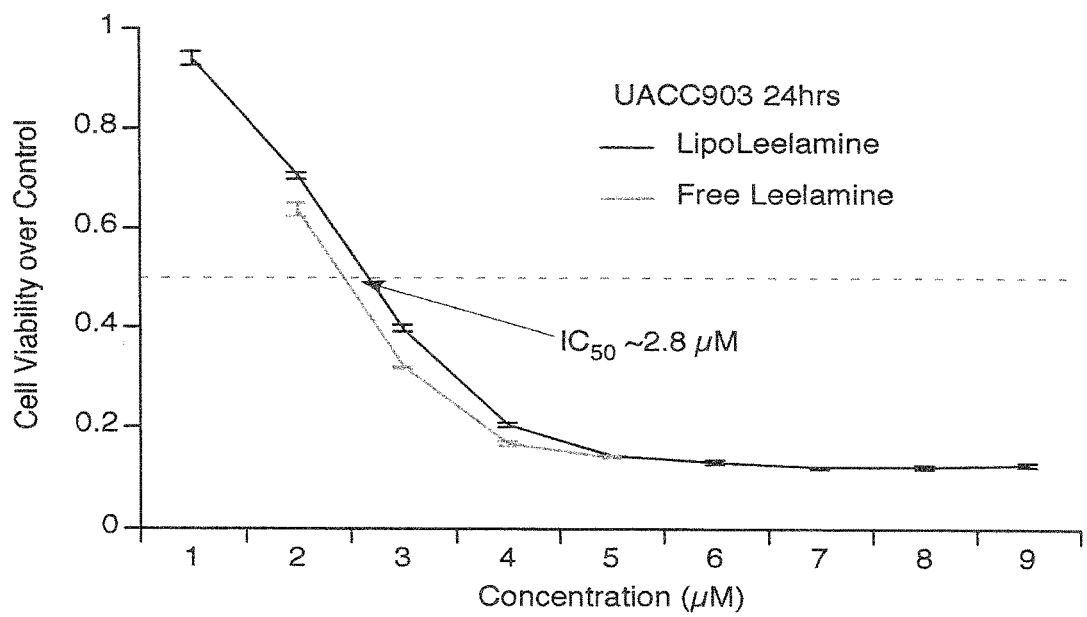
FIG. 28 is a graph showing the efficacy of liposomal formulation containing leelamine prepared at room temperature to inhibit melanoma cells compared to non-liposomal leelamine.

Nanolipolee generated at room temperature, as described above, has an efficacy comparable to the "naked" leelamine, i.e. non-liposomal leelamine, also called "free" leelamine herein. In this example, UACC 903 melanoma cells were treated with different concentrations of nanolipolee (1 μM-9 μM) and or "free" leelamine in DMSO (2 μM-5 μM). Nanolipolee was kept at room temperature during preparation of the nanoliposome. Cells were maintained in DMEM supplemented with 10% FBS and L-glutamine. After 24 h of treatment, an MTS assay was performed to determine the fractional cell viability relative to the DMSO control. $IC_{50}$ values were calculated using Graphpad Prism software. FIG. 28 is a graph that shows the efficacy of liposomal formulation containing leelamine prepared at room temperature to inhibit melanoma cells.

Figure 29:
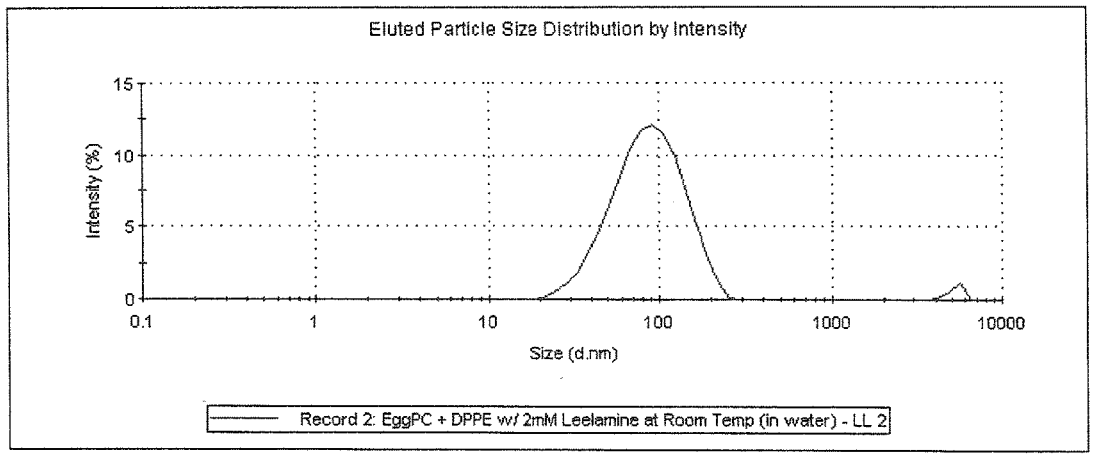
FIG. 29 is a graph showing the distribution of sizes of a nanoliposomes prepared at room temperature containing leelamine.
Figure 30:
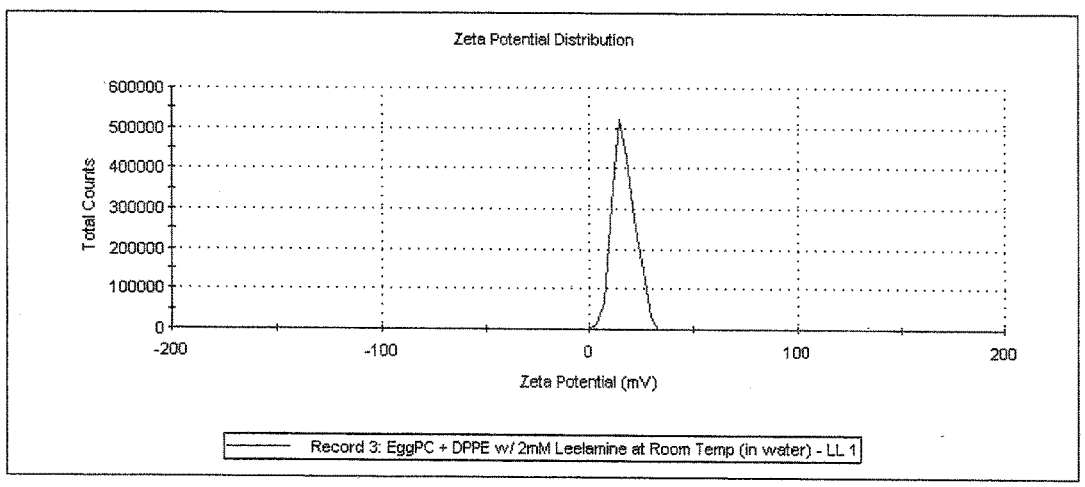
FIG. 30 is a graph showing the distribution of charge of nanoliposomes prepared at room temperature containing leelamine.

A Malvern Zetasizer was used to determine the mean nanolipolee particle size and the range of nanolipolee particle sizes as well as the mean nanolipolee particle charge as well as the range of nanolipolee particle charges. The mean size of nanolipolee generated using a room temperature procedure was determined to be 92.8 nm, and the mean charge was determined to be +16.8 mV. FIG. 29 is a graph showing the distribution of sizes of a nanoliposomes prepared at room temperature containing leelamine. The distribution of all particle sizes is shown, with a mean of 92.8 nm. FIG. 30 is a graph showing the distribution of charge of nanoliposomes prepared at room temperature containing leelamine. The distribution of all particle charges is shown, with a mean of +16.8 mV.

Nanoparticles containing both leelamine and ATK were generated, "nanoleelATK-999." In this example, a nanoliposome formulation of leelamine and ATK includes egg phosphatidylcholine (PC) and 1,2-Dipalmitoryl-sn-Glycero-3-Phosphoethanolamine (DPPE) conjugatged polyethylene glycol (+PEG). To prepare the nanoliposome formulation of this example, lipid stocks stored in a −20° C. freezer are retrieved and allowed to come to room temperature. A glass cuvette is used to prepare the lipid solution, ATK and leelamine in ethanol by first adding 20 mg of egg phosphatidylcholine (PC) and 5 mg of 1,2-dipalmitoryl-sn-glycero-3-phosphoethanolamine (DPPE) conjugatged polyethylene glycol (+PEG), adding ATK such that the final concentration of ATK in the nanoliposomal formulation is 10 mM and adding leelamine such that the final concentration of leelamine in the nanoliposomal formulation is 0.7 mM (1 mL final volume). Nitrogen gas is then passed over the material in the glass cuvette to evaporate chloroform and ethanol for at least 1 hour or until lipid is completely dry. Once the mixture is completely dry, 1 mL of solvent, in this case sterile water, is added and the resulting material is kept at room temperature. The top of the cuvette is covered and the material is mixed using a vortex mixer for 30 seconds on low setting every 15 minutes, at least 5 times. When the solution appears homogenous, it is sonicated in a room temperature water bath until the solution is transparent, a process that typically takes less than 5 minutes if the material has been sonicated properly. The resulting liposomal mixture is then extruded through a 100 μm filter 11 times. The resulting liposomal formulation of leelamine and ATK is transferred into a 1.5 mL falcon tube for long term storage at 4° C. In this example, the preparation of nanoliposomal leelamine and ATK, "nanoleelATK-999," was carried out entirely at room temperature due to the aforementioned instability of ATK at high temperatures.

Figure 31:
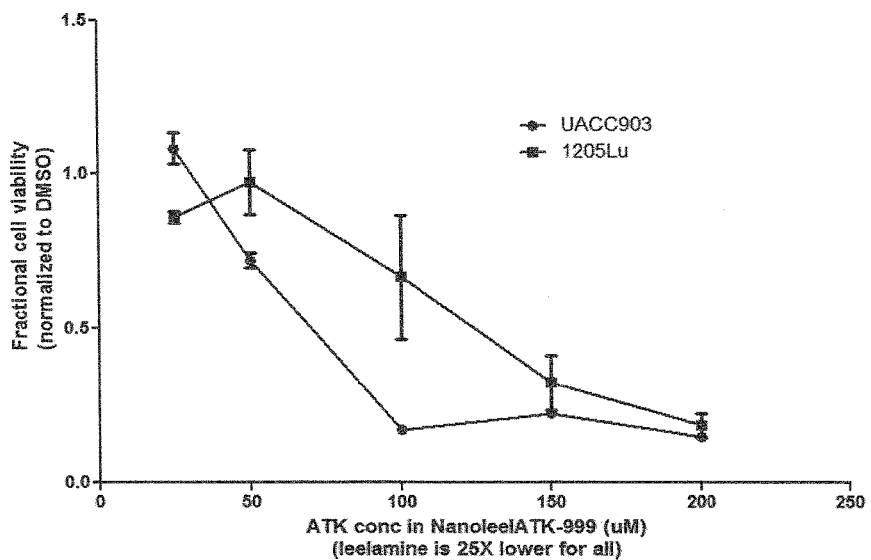
FIG. 31 is a graph showing efficacy of NanoleelATK-999 prepared with heating at 70° C. for 1 hour.

The instability of nanoleelATK-999 when prepared at 70° C. is shown in FIG. 31. The melanoma cell lines UACC 903 and 1205 Lu were treated with different concentrations of nanoleelATK999 which had been heated for 1 hour during preparation of the nanoliposomes. Cells were maintained in DMEM supplemented with 10% FBS and L-glutamine. After 24 hours of treatment, an MTS assay was performed to determine the fractional cell viability relative to the DMSO control. FIG. 31 is a graph showing efficacy of NanoleelATK-999 prepared with heating at 70° C. for 1 hour.

Figure 32:
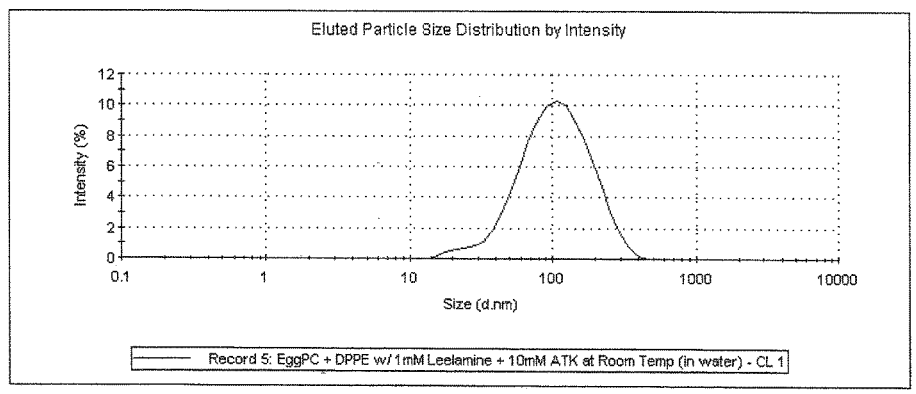
FIG. 32 is a graph showing the sizes of nanoliposomes prepared at room temperature containing leelamine and ATK.
Figure 33:
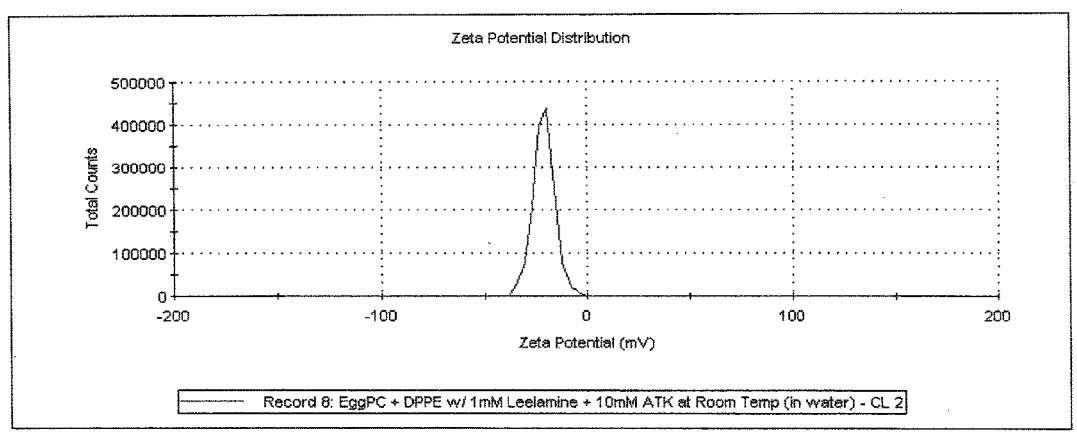
FIG. 33 is a graph showing the charges of nanoliposomes prepared at room temperature containing leelamine and ATK.

A Malvern Zetasizer was used to determine the distribution and mean nanoleelATK-999 particle sizes as well as the distribution and mean particle charges. The mean size of the nanoleelATK-999 particles was determined to be 118.2 nm, and the mean charge was determined to be −21.1 mV. FIG. 32 is a graph showing the sizes of nanoliposomes prepared at room temperature containing leelamine and ATK. The distribution of all particle sizes is shown, with a mean of 118.2 nm. FIG. 33 is a graph showing the charges of nanoliposomes prepared at room temperature containing leelamine and ATK. The distribution of all particle charges is shown, with a mean of −21.1 mV.

In-Vivo Treatment

Tumor kinetics will be measured by subcutaneous injection of $1 \times 10^6$ UACC 903 or 1205 Lu cells in 0.2 mL of DMEM supplemented with 10% FBS. Cells will be injected above both left and right rib cages of 3 to 4 week-old female Athymic-Foxn1$^{nu}$ nude mice (Harlan Sprague Dawley). Six days later, when a fully vascularized 50-75 mm$^3$ tumor will have formed, mice will be randomly divided into 7 different groups: Group 1 (empty liposomes (no drug) reconstituted in saline or water); Group 2 (ATK, 15 mg/kg bodyweight reconstituted in saline or water); Group 3 (leelamine, 0.75 mg/kg bodyweight reconstituted in saline or water); Group 4 (ATK, 15 mg/kg bodyweight reconstituted in saline or water); Group 5 (ATK 15 mg/kg bodyweight+leelamine 0.75 mg/kg bodyweight reconstituted in saline or water); Group 6 (ATK 15 mg/kg bodyweight+leelamine 1.5 mg/kg bodyweight reconstituted in saline or water) and will be treated intravenously on alternate days for 3-4 weeks (3 mice/group; 2 tumors/mouse). Body weight in grams and dimensions of developing tumors in mm$^3$ will be measured on alternate days.

Size and time match tumors for analysis of biological processes regulating tumor development. Effects of liposomes containing both leelamine and ATK delayed tumor development will be analyzed by comparing size and time matched xenografted melanoma tumors treated with empty control liposome or liposomes containing single or combined agents. $2.5 \times 10^6$ 1205 Lu cells will be injected s.c. into nude mice, generating tumors of the same size developing at parallel time points. Six days later, mice will be treated i.v. with empty liposomes, leelamine in saline, ATK in saline, Leelamine+ATK in salein, nanoliposomes containing leelamine or ATK alone or nanoliposomes containing both leelamine and ATK, daily for up to 15 days. Tumors will be harvested at days 11, 13 and 15 for comparison of rates of cellular proliferation, apoptosis and vessel density by immunohistochemistry. Cell proliferation will be measured using mouse anti-human Ki-67 staining from Pharmigen (San Diego, Calif.). Apoptosis rates will be determined using "terminal deoxynucleotidyl transferase-mediated dUTP nick end labeling (TUNEL)" TMR Red Apoptosis kit from Roche (Mannheim, Germany). Vessel density indicative of angiogenesis will be measured using a purified rat anti-mouse CD31 (PECAM-1) monoclonal antibody for immunostaining (Pharmingen). Number of Ki-67 or TUNEL stained cells will be quantified as the percentage of total cells in tumors using the IP Lab imaging software program. Areas containing vessels will be quantified and compared between tumor sections. For all tumor analyses, a minimum of 4-6 different tumors with 4-6 fields per tumor section will be analyzed and results represented as the average±SEM.

Toxicity assessments and histological analysis of organs. Animals from will be used to assess the toxicity associated with individual or combined agents. At the end of treatment with leelamine and ATK as described for xenograft mice, blood will be collected from each euthanized animal in a serum separator tube with lithium heparin (BD Microtainer) following cardiac puncture and analyzed for levels of GLU (Glucose), BUN (Blood urea nitrogen), CREA (Creatinine), Phosphate, TP (Total Protein), CAL (Calcium), GLO (Globulin), ALT (Alanine aminotransferase), ALKP (Alkaline phosphatase), TBIL (Total bilirubin), CHOL (Total cholesterol), TRIG (Total triglyceride), AST (Aspartate aminotransferase) and AMY (Amylase) to possible effects on vital organs such as liver, heart, kidney, and pancreas related toxicity. A portion of liver, heart, kidney, pancreas, spleen, intestine and stomach tissue from each animal will be formalin-fixed and paraffin-embedded to examine changes in cell morphology and tissue organization following hematoxylin/eosin staining.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A pharmaceutical composition, comprising: leelamine and arachidonyl trifluoromethyl ketone in a synergistic ratio in the range of 1:4-1:23 effective to decrease viability of melanoma cells; and a pharmaceutically acceptable carrier.

2. The pharmaceutical composition of claim 1, wherein the pharmaceutically acceptable carrier comprises liposomes.

3. The pharmaceutical composition of claim 2, wherein the liposomes have an average particle size in the range of 1 nm-500 nm.

4. The pharmaceutical composition of claim 1, wherein the leelamine is present in a concentration in the range of 0.1 micromolar-100 millimolar and the arachidonyl trifluoromethyl ketone is present in a concentration in the range of 0.1 micromolar-100 millimolar.

5. A method of treating melanoma in a subject in need thereof, comprising: administering, concurrently or sequentially, a therapeutically effective amount of leelamine and arachidonyl trifluoromethyl ketone in a synergistic ratio in the range of 1:4-1:23 to the subject.

6. The method of treating melanoma of claim 5, wherein administering the therapeutically effective amount of leelamine and arachidonyl trifluoromethyl ketone to the subject comprises administering liposomes containing leelamine and/or liposomes containing arachidonyl trifluoromethyl ketone.

7. The method of treating melanoma of claim 6, wherein the liposomes comprise at least one polyethylene glycol modified neutral lipid, wherein the amount of polyethylene glycol modified neutral lipid is an amount in the range of 2.5-30 molar percent, inclusive, of total lipids in the liposomes; and one or more anionic, cationic or neutral lipids in an amount in the range of 70-97.5, inclusive, molar percent of total lipids in the liposomes.

8. The method of treating melanoma of claim 5, wherein the leelamine is administered in a concentration in the range of 0.1 micromolar-100 millimolar and the arachidonyl trifluoromethyl ketone is administered in a concentration in the range of 0.1 micromolar-100 millimolar.

9. The method of treating melanoma of claim 5, wherein the subject is human.

10. The method of treating melanoma of claim 5, further comprising administration of an adjunct anti-cancer treatment.

11. The method of treating melanoma of claim 5, wherein the leelamine and arachidonyl trifluoromethyl ketone are administered by a route selected from: intravenous, intramuscular, subcutaneous, intraperitoneal, oral, otic, rectal, vaginal, topical, parenteral, pulmonary, ocular, nasal, intratumoral and mucosal.

12. The method of treating melanoma of claim 5, wherein the leelamine and arachidonyl trifluoromethyl ketone are administered by an intravenous route of administration.

13. The method of treating melanoma of claim 5, wherein the leelamine and arachidonyl trifluoromethyl ketone are administered intratumorally.

* * * * *